US011434299B2

(12) United States Patent
Force Aldred et al.

(10) Patent No.: US 11,434,299 B2
(45) Date of Patent: Sep. 6, 2022

(54) ANTI-BCMA HEAVY CHAIN-ONLY ANTIBODIES

(71) Applicant: TeneoBio, Inc., Newark, CA (US)

(72) Inventors: Shelley Force Aldred, Newark, CA (US); Nathan Trinklein, Newark, CA (US); Katherine E. Harris, Newark, CA (US); Kevin Dang, Newark, CA (US); Wim van Schooten, Newark, CA (US)

(73) Assignee: TeneoBio, Inc., Newark, CA (US)

( * ) Notice: Subject to any disclaimer, the term of this patent is extended or adjusted under 35 U.S.C. 154(b) by 0 days.

(21) Appl. No.: 16/472,173

(22) PCT Filed: Dec. 21, 2017

(86) PCT No.: PCT/US2017/067870
§ 371 (c)(1),
(2) Date: Jun. 20, 2019

(87) PCT Pub. No.: WO2018/119215
PCT Pub. Date: Jun. 28, 2018

(65) Prior Publication Data
US 2019/0352412 A1 Nov. 21, 2019

Related U.S. Application Data

(60) Provisional application No. 62/437,588, filed on Dec. 21, 2016.

(51) Int. Cl.
C07K 16/28 (2006.01)
(52) U.S. Cl.
CPC ...... C07K 16/2878 (2013.01); C07K 2317/21 (2013.01); C07K 2317/31 (2013.01); C07K 2317/565 (2013.01); C07K 2317/732 (2013.01); C07K 2317/92 (2013.01)
(58) Field of Classification Search
CPC .................................................. C07K 16/2878
See application file for complete search history.

(56) References Cited

U.S. PATENT DOCUMENTS

| 5,500,362 | A | 3/1996 | Robinson et al. |
|---|---|---|---|
| 5,585,097 | A | 12/1996 | Bolt et al. |
| 5,821,337 | A | 10/1998 | Carter et al. |
| 5,929,212 | A | 7/1999 | Jolliffe et al. |
| 5,968,509 | A | 10/1999 | Gorman et al. |
| 6,706,265 | B1 | 3/2004 | Bolt et al. |
| 6,750,325 | B1 | 6/2004 | Jolliffe et al. |
| 7,262,276 | B2 | 8/2007 | Huang et al. |
| 7,381,803 | B1 | 6/2008 | Weiner et al. |
| 7,541,513 | B2 | 6/2009 | Bruggeman et al. |
| 7,635,472 | B2 | 12/2009 | Kufer et al. |
| 7,728,114 | B2 | 6/2010 | Mach et al. |
| 7,862,813 | B2 | 1/2011 | Bjork et al. |
| 8,236,308 | B2 | 8/2012 | Kischel et al. |
| 8,367,888 | B2 | 2/2013 | Bruggemann et al. |
| 8,883,150 | B2 | 11/2014 | Craig et al. |
| 9,034,324 | B2 | 5/2015 | Kalled et al. |
| 9,150,664 | B2 | 10/2015 | Kufer et al. |
| 9,340,621 | B2 | 5/2016 | Kufer et al. |
| 9,365,655 | B2 | 6/2016 | Craig et al. |
| 2007/0065437 | A1 | 3/2007 | Elson et al. |
| 2007/0212733 | A1 | 9/2007 | Martin |
| 2009/0098134 | A1 | 4/2009 | Buelow |
| 2010/0122358 | A1 | 5/2010 | Bruggemann et al. |
| 2013/0156769 | A1 | 6/2013 | Kufer et al. |
| 2013/0273055 | A1 | 10/2013 | Borges et al. |
| 2013/0273066 | A1 | 10/2013 | Gokarn et al. |
| 2015/0118251 | A1 | 4/2015 | Deslandes |
| 2015/0266966 | A1 | 9/2015 | Smith et al. |
| 2015/0368351 | A1 | 12/2015 | Vu et al. |
| 2015/0376287 | A1 | 12/2015 | Vu et al. |
| 2016/0046724 | A1 | 2/2016 | Lee et al. |
| 2016/0166689 | A1 | 6/2016 | Adler et al. |
| 2016/0194399 | A1 | 7/2016 | Irving et al. |
| 2016/0355591 | A1 | 12/2016 | Goldenberg et al. |
| 2017/0051068 | A1 | 2/2017 | Pillarisetti et al. |
| 2019/0263904 | A1 | 8/2019 | Trinklein et al. |
| 2020/0048348 | A1 | 2/2020 | Trinklein et al. |
| 2020/0157232 | A1 | 5/2020 | Trinklein et al. |
| 2021/0340255 | A1 | 11/2021 | Harris et al. |
| 2022/0025047 | A1 | 1/2022 | Trinklein et al. |

FOREIGN PATENT DOCUMENTS

| CN | 105384825 | A | 3/2016 |
|---|---|---|---|
| EP | 1210425 | B1 | 4/2007 |
| EP | 1223964 | B1 | 4/2007 |
| EP | 1806143 | B1 | 6/2016 |

(Continued)

OTHER PUBLICATIONS

Rudikoff et al., Proc Natl Acad Sci USA. Mar. 1982;79(6):1979-83.*
Adams et al., "Prolonged in Vivo Tumour Retention of a Human Diabody Targeting the Extracellular Domain of Human HER2/neu," (1998) British Journal of Cancer 77(9):1405-1412.
Ali et al., "T cells expressing an anti-B-cell maturation antigen chimeric antigen receptor cause remissions of multiple myeloma," (2016) Blood 128(13):1688-1700.
Seckinger et al., "Target Expression, Generation, Preclinical Activity, and Pharmacokinetics of the BCMA-T Cell Bispecific Antibody EM801 for Multiple Myeloma Treatment," (2017) Cancer Cell, Cell Press US 31(3):396-410.

(Continued)

Primary Examiner — Prema M Mertz
(74) Attorney, Agent, or Firm — Benjamin C. Pelletier; Haynes Boone LLP

(57) ABSTRACT

Anti-BCMA heavy chain-only antibodies (HCAb) and disclosed, along with methods of making such antibodies, compositions, including pharmaceutical compositions, comprising such antibodies, and their use to treat B-cell disorders characterized by the expression of BCMA.

17 Claims, 7 Drawing Sheets
Specification includes a Sequence Listing.

(56) References Cited

FOREIGN PATENT DOCUMENTS

| | | | |
|---|---|---|---|
| EP | 2780374 B1 | 8/2019 | |
| EP | 2780375 B1 | 9/2019 | |
| WO | 1996/027011 A1 | 9/1996 | |
| WO | 1998/050431 A2 | 11/1998 | |
| WO | 2000/040716 A2 | 7/2000 | |
| WO | 2001/012812 A2 | 2/2001 | |
| WO | 2001/024811 A1 | 4/2001 | |
| WO | 2001/024812 A1 | 4/2001 | |
| WO | 2001/087977 A2 | 11/2001 | |
| WO | 2002/066516 A2 | 8/2002 | |
| WO | 2004/106383 A1 | 12/2004 | |
| WO | 2005/040220 A1 | 5/2005 | |
| WO | 2005/061547 A2 | 7/2005 | |
| WO | 2006/008548 A2 | 1/2006 | |
| WO | 2007/042261 A2 | 4/2007 | |
| WO | 2007/066109 A1 | 6/2007 | |
| WO | 2007/117600 A2 | 10/2007 | |
| WO | 2008/119565 A2 | 10/2008 | |
| WO | 2008/119566 A2 | 10/2008 | |
| WO | 2008/119567 A2 | 10/2008 | |
| WO | 2009/132058 A2 | 10/2009 | |
| WO | 2010/037835 A2 | 4/2010 | |
| WO | 2010/037836 A2 | 4/2010 | |
| WO | 2010/037837 A2 | 4/2010 | |
| WO | 2010/037838 A2 | 4/2010 | |
| WO | 2010/104949 A2 | 9/2010 | |
| WO | 2010/109165 A2 | 9/2010 | |
| WO | 2012/066058 A1 | 5/2012 | |
| WO | 2012066058 A1 | 5/2012 | |
| WO | 2012/122512 A1 | 9/2012 | |
| WO | 2012/143498 A1 | 10/2012 | |
| WO | 2012143498 A1 | 10/2012 | |
| WO | 2012163805 A1 | 12/2012 | |
| WO | 2013/072406 A1 | 5/2013 | |
| WO | 2013/072415 A1 | 5/2013 | |
| WO | 2014/068079 A1 | 5/2014 | |
| WO | 2014/089335 A2 | 6/2014 | |
| WO | 2014/122144 A1 | 8/2014 | |
| WO | 2015/149077 A1 | 10/2015 | |
| WO | 2016/062990 A1 | 4/2016 | |
| WO | 2016094304 A2 | 6/2016 | |
| WO | 2016/113555 A1 | 7/2016 | |
| WO | 2016/187546 A1 | 11/2016 | |
| WO | 2017/025038 A1 | 2/2017 | |
| WO | 2017/031104 A1 | 2/2017 | |
| WO | 2015/063339 A1 | 5/2017 | |
| WO | 2017/081211 A2 | 5/2017 | |
| WO | 2017/223111 A1 | 12/2017 | |
| WO | 2018/039180 A1 | 3/2018 | |
| WO | 2018/052503 A1 | 3/2018 | |
| WO | 2018/237006 A1 | 12/2018 | |
| WO | 2018/237037 A2 | 12/2018 | |
| WO | 2019/000223 A1 | 1/2019 | |
| WO | 2019/133761 A1 | 7/2019 | |

OTHER PUBLICATIONS

Anonymous, "Flow Cytometry Antibody: CD3e Cat. No. CT026-R301, SinoBiological Inc,—Antibody-Catalogue," (2017) Sinobiological, Inc. Retrieved from Internet: URL http://www.sinobiologica.com/flow-cytometry-antibody-elite.html.

Arnett et al., "Crystal Structure of a Human CD3-epsilon/delta Dimer in Complex with a UCHT1 Single-chain Antibody Fragment," (2004) Proc Natl Acad Sci USA 101(46):16268-16273.

Baas et al., "Superhuman Mice," (2014) Science-Business exchange 7(17):1-2.

Borchmann et al., "Phase 1 trial of the Novel Bispecific Molecule H22xKi-4 in Patients with Refractory Hodgkin Lymphoma," (2002) Blood 100(9):3101-3107.

Bruggemann et al., "Heavy-Chain-Only Antibody Expression and B-Cell Development in the Mouse," (2006) Crit. Rev. Immunol. 26(5):377-390.

Buelow et al., "Development of a fully human T cell engaging bispecific antibody for the treatment of multiple myeloma," (2017) J Clin Oncol vol. 35 Supplement.

Carpenter et al., "B-cell Maturation Antigen Is a Promising Target for Adoptive T-cell Therapy of Multiple Myeloma," (2013) Clin Cancer Res 19(8):2048-2060.

Christian et al., "Measuring Bacterial Ectoenzyme Activities in Marine Waters Using Mercuric Chloride as a Preservative and Control," (1995) Marine Ecology Progress Series 123:217-224.

Dai et al., "Chimeric Antigen Receptors Modified T-Cells for Cancer Therapy," (2016) J Natl Cancer Inst 108(7):dvj439.

Dooley et al., "Selection and Characterization of Naturally Occurring Single-domain (IgNAR) Antibody Fragments from Immunized Sharks by Phage Display," (2003) Molecular Immunology 40(1):25-33.

Desmyter et al., "Antigen Specificity and High Affinity Binding Provided by One Single Loop of a Camel Single-domain Antibody," (2001) Journal of Biological Chemistry, American Society for Biochemistry and Molecular Biology 276(28):26285-26290.

Durben et al., "Characterization of a Bispecific FLT3 X CD3 Antibody in an Improved, Recombinant Format for the Treatment of Leukemia," (2015) Molecular Therapy 23(4):648-655.

Frenken et al., Isolation of Antigen Specific Llama $V_{HH}$ Antibody Fragments and Their High Level Secretion by *Saccharomyces cerevisiae*, (2000) J. Biotechnol. 78:11-21.

Gershoni et al., "Epitope Mapping—The First Step in Developing Epitope-based Vaccines," (2007) Biodrugs, Adis International, Ltd. NZ 21(3):145-156.

Geurts et al., "Knockout Rats via Embryo Microinjection of Zinc-Finger Nucleases,"(2009) Science 325(5939):433.

Ghahroudi et al., "Selection and Identification of Single Domain Antibody Fragments from Camel Heavy-chain Antibodies," (1997) FEBS Lett. 414:521-526.

Glennie et al., "Preparation and Performance of Bispecific F(ab' gamma)2 Antibody Containing Thioether-linked Fab' gamma Fragments," (1987) Journal of Immunology 139(7):2367-2375.

Gras et al., "BCMAp: an integral membrane protein in the Golgi apparatus of human mature B lymphocytes," (1995) Int. Immunol. 7(7):1093-1106.

Hamers-Casterman et al., "Naturally Occurring Antibodies Devoid of Light Chains,"(1993) Nature 363:446-448.

Hipp et al., "A Novel BCMA/CD3 Bispecific T-cell Engager for the Treatment of Multiple Myeloma Induces Selective Lysis in Vitro and in Vivo," (2016) 31(8):1743-1751.

Hotzel et al., "A strategy for risk mitigation of antibodies with fast clearance," (2012) mABs 4(6):753-760.

Iri-Sofla et al., "Nanobody-based chimeric receptor gene integration in Jurkat cells mediated by PhiC31 integrase," (2011) Experimental Cell Research 317(18):2630-2641.

Jackson et al., "Driving CAR T-cells forward," (2016) Nature Reviews Clinical Oncology 13:370—Jackson et al., "Driving CAR T-cells forward," (2016) Nature Reviews Clinical Oncology 13:370-383383.

Jamnani et al., "T cells expressing VHH-directed oligoclonal chimeric HER2 antigen receptors: Towards tumor-directed oligoclonal T cell therapy," (2014) Biochim Biophys Acta 1840(1):378-386.

Janssens et al., "Generation of Heavy-chain-only Antibodies in Mice," (2006) Proceedings of the National Academy of Sciences of the USA 103(41):15130-15135.

Jaton et al., "Recovery of antibody activity on reoxidation of completely reduced polyalanyl heavy chain and its Fd fragment derived from anti-2,4-dinitrophenyl antibody,"(1968) Biochemistry 7(12):4185-4195.

Lindhofer et al., "Preferential Species-restricted Heavy/Light Chain Pairing in Rat/Mouse Quadromas. Implications for a Single-step Purification of Bispecific Antibodies," The Journal of Immunology, 155(1):219-225.

Link et al., "Anti-CD3-Based Bispecific Antibody Designed for Therapy of Human B-Cell Malignancy can Induce T-cell Activation by Antigen-dependent and Antigen-independent Mechanisms," (1998) Int. J. Cancer 77:251-256.

(56) References Cited

OTHER PUBLICATIONS

Mack et al., "A Small Bispecific Antibody Construct Expressed as a Functional Single-chain Molecule with High Tumor Cell Cytotoxicity," (1995) PNAS 92:7021-7025.
Muyldermans "Single domain camel antibodies: current status," (2001) J Biotechnol 74(4):277-302.
Nguyen et al., "Heavy-chain Only Antibodies Derived from Dromedary are Secreted and Displayed by Mouse B Cells," (2003) Immunology 109(1):93-101.
Nuttall et al., "Isolation and Characterization of an IgNAR Variable Domain Specific for the Human Mitochondrial Translocase Receptor Tom70," (2003) Eur. J. Biochem. 270:3543-3554.
Nuttall et al., "Selection and Affinity Maturation of IgNAR Variable Domains Targeting Plasmodium Falciparum AMA1," (2004) Function and Bioinformatics 55:187-197.
Revets et al., "Nanobodies as novel agents for cancer therapy," (2005) Expert Opin Biol Ther 5(1):111-124.
Ridgway et al., "'Knobs-into-holes' Engineering of Antibody CH3 Domains for Heavy Chain Heterodimerization," (1996) Protein Engineering 9(7):617-621.
Rossi et al., "Redirected T-cell Killing of Solid Cancers Targeted with an Anti-CD3/Trop-2-Bispecific Antibody is Enhanced in Combination with Interferon-g," 2014 Molecular Cancer Therapeutics 13(10):2341-2351.
Salmeron et al., "A conformational epitope expressed upon association of CD3-epsilon with either CD3-delta or CD3-gamma is the main target for recognition by anti-CD3 monoclonal antibodies." (1991) J. Immunol 147(9):3047-3052.
Sanz et al., "B cells as therapeutic targets in SLE" (2010) Nat Rev Rheumatol 6:326-337.
Sitia et al., "Developmental regulation of IgM secretion: The role of the carboxy-terminal cysteine," (1990) Cell 60(5):781-790.
Tai et al., "APRIL and BCMA promote human multiple myeloma growth and immunosuppression in the bone marrow microenvironment," (2016) Blood 127(25):3225-3236.
Tai et al., "Novel anti-B-cell maturation antigen antibody-drug conjugate (GSK2857916) selectively induces killing of multiple myeloma," (2014) Blood 123(20):3128-3138.
Trinklein et al., "Abstract LB-090: Sequence-based Discovery of Fully Human Anti-CD3 and Anti-PDL1 Single Domain Antibodies Using Novel Transgenic Rats," (2016) Cancer Research 76(14 Suppl).
Van der Linden et al., "Comparison of Physical Chemical Properties of Llama VHH Antibody Fragments and Mouse Monoclonal Antibodies," (1999) Biochim. Biophys. Acta. 1431(1):37-46.
Wu et al., "Simultaneous Targeting of Multiple Disease Mediators by a Dual-variable-domain Immunoglobulin," (2007) Nature Biotechnology 25:1290-1297.
Yoon et al., "Both High and Low Avidity Antibodies to the T Cell Receptor can have Agonist Activity," (1994) Immunity 1(7):563-569.
Zou et al., "Heavy chain—only antibodies are spontaneously produced in light chain-deficient mice," (2007) J Exp Med 204(13):3271-3283.
Anonymous: "A Clinical Study of Legend Biotech BCMA-chimeric Antigen Receptor Technology in Treating Relapsed/Refractory (R/R) Multiple Myeloma Patients," (2017) Clinical Trials.gov, retrieved from the Internet at URL https://clinicaltrials.gov/ct2/history/NCT030906597V_1 =View#StudyPageTop.
Rouet et al., "Fully Human VH Single Domains That Rival the Stability and Cleft Recognition of Camelid Antibodies," (2015) Journal of Biological Chemistry 290(19):11905-11917.
Ryan et al., "Antibody Targeting of B-cell Maturation Antigen on Malignant Plasma Cells," (2007) Molecular Cancer Therapeutics 6(11):3009-3018.
Ryan et al., "Antibody targeting of B-cell1 maturation antigen on malignant plasma cells,"(2007) Mol Cancer Ther6(11):3009-3018.
Kontermann, "Invited review—Recombinant bispecific antibodies for cancer therapy," (2005) Acta Pharmacologica Sinica 26(1):1-9.
Novak et al., "Expression of BCMA, TACI, and BAFF-R in multiple myeloma: a mechanism for growth and survival," (2004) Blood 103(2):689-694.
Sequence Listing of PCT Publication No. WO 2009/132058 (D2), published Oct. 29, 2009.
BCMA (Vicky-1): sc-57037 datasheet, Santa Cruz Biotechnology, https://datasheets.scbt.com/sc-57037.pdf (last visited Apr. 12, 2022).
BCMA (Vicky-1): ALX-804-151 product datasheet, Enzo Life Sciences, last revised Dec. 20, 2019.
MAB193 data sheet, Human BCMA/TNFRSF17 Antibody, R&D Systems, last revised Feb. 7, 2018.
Hipp et al., "A novel BCMA/CD3 bispecific T-cell engager for the treatment of multiple myeloma induces selective lysis in vitro and in vivo," (2017) Leukemia 31:1743-1751.
Sequence Listing of PCT Publication WO 2008/119567 (D14), published Oct. 9, 2008.
GenBank Accession No. AB052772.1, "*Homo sapiens* gene for BCMA, complete cds," available at https://www.ncbi.nlm.nih.gov/nuccore/AB052772 (last visited Apr. 23, 2020).
Sequence listing of PCT Publication No. WO 2010/104949 (D21), published Sep. 16, 2010.
Fitzgerald et al., "The Cytokine FactsBook," 2nd ed. (2001) Academic Press, pp. 151-152.
Bossen et al., "Review, BAFF, APRIL and their receptors: Structure, function and signaling," (2006) Seminars in Immunology 18:263-275.
Bodmer et al., "Review—The molecular architecture of the TNF superfamily," (2002) Trends in Biochemical Sciences 27(1):19-26.
Hymowitz et al., "Structures of APRIL-Receptor Complexes," (2005) Journal of Biological Chemistry 280(8):7218-7227.
Liu et al., "Ligand-receptor binding revealed by the TNF family member TALL-1," (2003) Nature 423:49-56.
Wallweber et al., "The Crystal Structure of A Proliferation-inducing Ligand, APRIL," (2004) Journal of Molecular Biology 343:283-290.
Patel et al., "Engineering an APRIL-specific B Cell Maturation Antigen," (2004) Journal of Biological Chemistry 279(16):16727-16735.
Vidal-Laliena et al., "Characterization of antibodies submitted to the B cell section of the 8th human leukocyte differentiation antigens workshop by flow cytometry and immunohistochemistry," (2005) Cellular Immunology 236:6-16.
Moreaux et al., "APRIL and TACI interact with syndecan-1 on the surface of multiple myeloma cells to form an essential survival loop," (2009) Eur J Heamatol 83:119-129.
Bellucci et al., "Graft-versus-tumor response in patients with multiple myeloma is associated with antibody response to BCMA, a plasma-cell membrane receptor," (2005) Blood 105(10):3945-3950.
Bellucci et al., "Complete response to donor lymphocyte infusion in multiple myeloma is associated with antibody responses to highly expressed antigens," (2004) Blood 103(2):656-663.
Leiba et al., "Activation of B cell maturation antigen (BCMA) on human multiple myeloma cells by a proliferation-inducing ligand (APRIL) promotes myeloma cell function in the bone marrow microenvironment," (2007) Blood 110(11):1503.
Bellucci et al., "Complete response to donor lymphocyte infusion in patients with multiple myeloma is associated with antibody response to BCMA, a plasma cell membrane receptor,"(2003) Blood 102(11):192a-193a.
Tarte et al., "BAFF is a survival factor for multiple myeloma cells," (2002) Myeloma Biology II, p. 811a (Abstract #3203).
Dillon et al., "An APRIL to remember: Novel TNF ligands as therapeutic targets," (2006) Nat Rev 5:235-246.
Kontermann "Bispecific Antibodies" (2011) Springer-Verlag Berlin Heidelberg, Chapters 1, 2, 7, 11, 13, 14 and 15.
Choi et al., "Bispecific antibodies engage T-cells for antitumor Immunotherapy," (2011) Expert Opinion on Biological Therapy 11(7):843-853.
Müller et al., "Bispecific antibodies for cancer immunotherapy," (2010) Biodrugs 24(2):89-98.
Thakur et al., "Cancer therapy with bispecific antibodies: Clinical experience," (2010) Current Opinion in Molecular Therapeutics 12(3):340-349.

(56) References Cited

OTHER PUBLICATIONS

Chames et al., "Bispecific antibodies for cancer therapy," (2009) Current Opinion in Drug Discovery & Development 12(2):276-283.
Baeuerle et al., "Bispecific T-cell engaging antibodies for cancer therapy," (2009) Cancer Research 69(12):4941-4944.
Baeuerle et al., "BiTE: Teaching antibodies to engage T-cells for cancer therapy," (2009) Current Opinion in Molecular Therapeutics 11(1):22-30.
Baeuerle et al., "BiTE: A new class of antibodies that recruit T-cells," (2008) Drugs of the Future 33(2):137-147.
Muller et al., "Recombinant bispecific antibodies for cellular cancer immunotherapy," K2006) Current Opinion in Molecular Therapeutics 9(4):319-326.
Kufer et al., "Review—A revival of bispecific antibodies," (2004) Trends in Biotechnology 22(5):238-244.
GenBank Accession No. NM_000733, "*Homo sapiens* CD3e molecule (CD3E), mRNA", available at https://www.ncbi.nlm.nih.gov/nuccore/NM_000733.3 (last visited Apr. 23, 2020).
Panowski et al., "Preclinical efficacy and safety comparison of CD3 bispecific and ADC modalities targeting BCMA for the treatment of multiple myeloma," (2019) AACR OF1-OF13.
Declaration of Dr. Rui Zhu, PhD, dated Jun. 9, 2020 in EP Opposition No. 3428193 for EP Application No. 18187373.8.
Declaration of Kevin C. Lindquist in EP Opposition No. 3428193 for EP Application No. 18187373.8.
Excerpt of examination report from EP Application No. 12805432.7, dated Oct. 31, 2016, p. 1.
Patentee's Response to EP Communication under Article 94(3), dated May 10, 2017 in EP Application No. 12805432.7.
Patentee's Response to EP Communication under Article 94(3), dated Apr. 13, 2016 in EP Application No. 12805432.7.
Rennert et al., "A Soluble Form of B Cell Maturation Antigen, a Receptor for the Tumor Necrosis Factor Family Member APRIL, Inhibits Tumor Cell Growth," (2000) J. Exp. Med. 192(11):1677-1683.
Declaration Nathan D. Trinklein, Ph.D. in EP Opposition No. 3428193 for EP Application No. 18187373.8.
Kuhns et al., "Deconstructing the Form and Function of the RCR/CD3 Complex," (2006) Immunity 24:133-139.
Koarada et al., "Autoantibody-Producing RP105 B Cells, from Patients with Systematic Lupus Erythematosus, showed more Preferential Expression of BCMA Compared with BAFF-R than Normal Subject," (2010) Rheumatology 49:662-670.
Pelekanou et al., "Expression of TNF-superfamily members BAFF and APRIL in Breast Cancer: Immunohistochemical Study in 52 Invasive Ductal Breast Carcinomas," (2008) BMC Cancer 8(76):1-9.
Guy et al., "Organization of Proximal Signal at the TCR:CD3 Complex," (2009) Immunol Rev 232(1):1-22.
Proprietor's Remarks in Response to Office Action dated Jun. 19, 2014 in U.S. Pat. No. 9150664.
Proprietor's Remarks in Response to Office Action dated Dec. 16, 2014 in U.S. Pat. No. 9340621.
Kjer-Nielsen et al., "Crystal Structure of the Human T Cell Receptor CD3 εγ Heterodimer Complexed to the Therapeutic mAb OKT3," (2004) Proceedings of the National Academy of Sciences 101:7675-7680.
Chames et al., "Bispecific Antibodies for Cancer Therapy," (2009) mAbs 1(6):539-547.
Clayton et al., "CD3eta and CD3zeta are alternatively spliced products of a common genetic locus and are transcriptionally and/or post-transcriptionally regulated during T-cell development," (1991) Proceedings of the National Academy of Sciences USA 88:5202-5206.
Neisig et al., "Assembly of the T-Cell Antigen Receptor," (1993) Journal of Immunology 151:870-879.
Bargou et al., "Tumor Regression in Cancer Patients by Very Low Doses of a T Cell-Engaging Antibody," (2008) Science 321:974-977.

Honemann et al., "A Novel Recombinant Bispecific Single-chain Antibody, bscWue-1 x CD3, Induces T-cell-mediated Cytotoxicity Towards Human Multiple Myeloma Cells," (2004) Leukemia 15:636-644.
Wayback machine snapshot of BCMA UniprotKB/Swiss-Prot entry, Aug. 3, 2011 https://web.archive.org/web/20110803071256/ https://www.uniprot.orq/uniprot/Q02223.
Gruss et al., "Structural and Biological Features of the TNF Receptor and TNF Ligand Superfamilies: Interactive Signals in the Pathobiology of Hodgkin's Disease," (1996) Ann Oncol, 7 (Suppl 4):19-26.
Liu et al., "Ligand-receptor Binding Revealed by the TNF Family Member TALL-1," (2003) Nature 423(6935):49-5.
Levine, "Mechanisms of Soluble Cytokine Generation," (2004) J Immunol 173(9):5343-8.
Reichert et al., "Development Trends for Monoclonal Antibody Cancer Therapeutics," (2007) Nat Rev Drug Discov 6(5):349-356.
Sanchez et al., "Serum B-cell Maturation Antigen Elevated in Multiple Myeloma and Correlates with Disease Status and Survival," (2012) Br J Haematol 158(6):727-738.
Topp et al., "Anti-B-Cell Maturation Antigen BiTE Molecule AMG 420 Induces Responses in Multiple Myeloma," (2020) J Clin Oncol 38(8):775-783.
Statutory Declaration of Dr. Robert Sailer, Executive Director Program Management at Amgen Research (Munich) GmbH (Vice President R&D Operations & Planning in Jan. 2011).
Kapoor et al., "Anti-CD20 Monoclonal Antibody Therapy in Multiple Myeloma," (2008) Br J Haematol 141(2):135-148.
Figure 6.8 of Antigen receptor structure and signaling pathways, Immunobiology: The Immune System in Health and Disease. 5th Edition, Janeway CA Jr, Travers P, Walport M, et al., New York: Garland Science; 2001.
Declaration of Kara Olson, dated May 14, 2021 in EP Opposition No. 3428193 for EP Application No. 18187373.8.
Bluemel et al., "Epitope Distance to the Target Cell Membrane and Antigen Size Determine the Potency of T Cell-mediated Lysis by BiTE Antibodies Specific for a Large Melanoma Surface Antigen," (2010) Cancer Immunol Immunother 59:1197-1209.
Verkleij et al., "T-Cell Redirecting Bispecific Antibodies Targeting BCMA for the Treatment of Multiple Myeloma," (2020) Oncotarget 11(45):4076-4081.
Tai et al., "Novel Anti-B-Cell Maturation Antigen Antibody-drug Conjugate (GSK2857916) Selectively Induces Killing of Multiple Myeloma," (2014) Blood 123(20):3128-38.
Zou et al., "Heavy Chain-Only Antibodies are Spontaneously Produced in Light Chain-Deficient," (2007) J Exp Med 204(13):3271-3283.
Chothia et al., "Canonical structures for the hypervariable regions of immunoglobulins," (1987) Journal of Molecular Biology 196(4):901-917.
Zhao et al., "A germline knowledge based computational approach for determining antibody complementarity determining regions," (2010) Molecular Immunology 47(4):694-700.
Chothia et al., "Conformations of immunoglobulin hypervariable regions," (1989) Nature 342:877-883.
Honegger, "Yet Another numbering scheme for immunoglobulin variable domains: an automatic modeling and analysis tool," (2001) Journal of Molecular Biology 309(3):657-670.
Ofran et al. "Automated identification of complementarity determining regions (CD Rs) reveals peculiar characteristics of CDRs and B cell epitopes," (2008) J Immunol 181:6230-6235.
Almagro, "Identification of differences in the specificity-determining residues of antibodies that recognize antigens of different size: implications for the rational design of antibody repertoires," (2004) J Mol Recognit 17:132-143.
Padlan et al. "Identification of specificity-determining residues in antibodies," (1995) FASEB J 9:133-139.
Ravetch et al., "Fc Receptors," (1991) Annual Review of Immunology 9:457-492.
Clynes et al., "Fc Receptors are Required in Passive and Active Immunity to Melanoma," (1998) PNAS (USA) 95(2):652-656.

(56) References Cited

OTHER PUBLICATIONS

Gazzano-Santoro et al., "A Non-radioactive Complement-dependent Assay for Anti-CD20 Monoclonal Antibody," (1997) J Immunol. Methods 202:163.
Concepcion et al., "Label-Free Detection of Biomolecular Interactions Using BioLayer Interferometry for Kinetic Characterization," (2009) Combinatorial Chemistry & High Throughput Screening 12(8):791-800.
Langer, "New Methods of Drug Delivery," (1990) Science 249(4976):1527-1533.
Nguyen et al., "Functional Heavy-Chain Antibodies in Camelidae," (2001) Advances in Immunology 79:261-296.
Qin et al., "Paralleled comparison of vectors for the generation of CAR-T cells," (2016) Anti-Cancer Drugs 27(8):711-722.
Caraccio et al., "Bispecific Antibodies for Multiple Myeloma: A Review of Targets, Drugs, Clinical Trials and Future Directions," (2020) Frontiers in Immunology 11(50):1-25.
Jemal et al., "Cancer Statistics, 2008," ACS Journals (2008) 58(2):71-96.
Waxman et al., "Racial disparities in incidence and outcome in multiple myeloma: a population-based study," (2010) Blood 116(25):5501-5506.
Pulte et al., "Improvement in Survival of Older Adults with Multiple Myeloma: Results of an Updated Period Analysis of SEER Data," (2011) The Oncologist 16(11):1600-1603.
Kumar et al., "Improved survival in multiple myeloma and the impact of novel therapies," (2008) Blood 111(5):2516-2520.
Tueresson et al., "Patterns of Improved Survival in Patients with Multiple Myeloma in the Twenty-First Century: A Population-Based Study," (2010) Journal of Clinical Oncology 28(5):830-834.
Palumbo et al., "Daratumumab, Bortezomib, and Dexamethasone for Multiple Myeloma," (2016) New England Journal of Medicine 375(8):754-766.
Dimopoulos et al., "Daratumumab, Lenalidomide, and Dexamethasone for Multiple Myeloma," (2016) New England Journal of Medicine 375(14):1319-1331.
Mikkilineni et al., "Chimeric antigen receptor T-cell therapies for multiple myeloma," (2017) Blood 130(24):2594-2602.
Pick et al., "Daratumumab resistance is frequent in advanced-stage multiple myeloma patients irrespective of CD38 expression and is related to dismal prognosis," (2018) European Journal of Haematology 100(5):494-501.
Miller et al., "Design, Construction, and In Vitro Analyses of Multivalent Antibodies," (2003) Journal of Immunology 170(9):4854-4861.
Chen et al., "Fusion protein linkers: Property, design and functionality," (2013) Advanced Health Care Materials 65(10):1357-1369.
Buelow et al., "TNB3838.0001: A Multicenter, Phase 1, Open-Label, Dose-Escalation Andexpansion Study of TNB-3838, a Bispecific Antibodytargeting BCMA in Subjects with Relapsed or Refractorymultiple Myeloma," (2019) Blood 134(Supplement 1):1874.
DiLillo et al., "A BCMAxCD3 Bispecific T Cell-engaging Antibody Demonstrates Robust Antitumor Efficacy Similar to that of Anti-BCMA CAR T Cells," (2020) Blood Advances 5(5):1291-1304.
Hlavacek et al., "Steric Effects on Multivalent Ligand-Receptor Binding: Exclusion of Ligand Sites by Bound Cell Surface Receptors," (1999) Biophysical Journal 76(6):3031-3043.
Plückthun et al., "New protein engineering approaches to multivalent and bispecific antibody fragments," (1997) Immunology 3(2):83-105.
Sitia et al., "Developmental Regulation of IgM Secretion: The Role of the Carbosy-terminal Cysteine," (1990) Cell, 60:781-790.
Van der Linden et al., "Comparison of Physical Chemical Properties of Llama VHH Antibody Fragments and Mouse Monoclonal Antibodies," (1999) Biochimica et Biophysica Acta 1431:37-46.
Gust et al., "Endothelial Activation and Blood-Brain Barrier Disruption in Neurotoxicity after Adoptive Immunotherapy with CD19 Car-T Cells," (2017) Cancer Discovery 7(12):1405-1419.
Giavridis et al., "Car T cell-induced cytokine release syndrome is mediated by macrophages and abated by IL-1 blockade," (2018) Nature Medicine 24:731-738.
Anonymous (TeneoBio, Inc.), "A Study of TNB-383B in Subjects with Relapsed or Refractory Multiple Myeloma," (2019) retrieved from the Internet on May 1, 2019 from URL:https://clinicaltrials.gov/ct2/show/NCT03933735, 4 pages.
Norelli et al., "Monocyte-derived IL-1 and IL-6 are differentially required for cytokine-release syndrome and neurotoxicity due to CAR T cells," (2018) Nature Medicine24:739-748.
Fry et al., "CD22-targeted CAR T Cells Induce Remission in B-ALL that is Naïve or Resistant to CD19-targeted CAR Immunotherapy," (2018) Nature Medicine 24(1):20-28.
Nishimoto et al., "Adoptive Therapy with Cord Blood T Reglatory Cells Enhances Anti-myeloma Efficacy of T Cell Based Immunotherapies," (2020) Blood 136(Suppl); 26-27.
Rodriguez et al., "Initial Resulst of a Phase I Study of TNB-383B, a BCMA x CD3 Bispecific T-Cell Redirecting Antibody, in Relapsed/Refracotry Multiple Myeloma," (2020) Blood 136 (Supp 1):43-44.
Ryan et al., "Antibody Targeting of B-Cell Maturation Antigen on Malignant Plasma Cells," (2007) Mol Cancer Ther 6(11 ):3009-3018.
Van Schooten et al., "A Novel CD3/BCMA Bispecific Antibody Selectively Kills Plasma Cells in Bone Marrow of Healthy Individuals with Improved Safety," (2019) Lupus Science and Medicine 6(Supp 1):Abstract 293.
Kim et al., "Mutational Approaches to Improve the Biophysical Properties of Human Single-domain Antibodies," (2014) Biochimica et Biophysica Acta 1844:1983-2001.

* cited by examiner

| CLONE ID | MFI/bkgrd (H929 cell bind) | seq_aa_CDR1 | seq_aa_CDR2 | seq_aa_CDR3 |
|---|---|---|---|---|
| 308607 | 558.6 | GFTFSSYA (SEQ ID NO: 1) | ISGSGGST (SEQ ID NO: 5) | VKDWNTTMITE (SEQ ID NO: 19) |
| 308915 | 284.8 | GFTFTNYA (SEQ ID NO: 2) | ISGGGGST (SEQ ID NO: 54) | VKDWNTTMITE (SEQ ID NO: 19) |
| 314189 | 123.5 | GFTFSSYA (SEQ ID NO: 1) | ITENGGST (SEQ ID NO: 6) | VKDWNTTMITE (SEQ ID NO: 19) |
| 314196 | 133.6 | GFTFSSYA (SEQ ID NO: 1) | ITGDGGST (SEQ ID NO: 7) | VKDWNTTMITE (SEQ ID NO: 19) |
| 314201 | 76.9 | GFTFSSYA (SEQ ID NO: 1) | IIGSGGST (SEQ ID NO: 8) | VKDWNTTMITE (SEQ ID NO: 19) |
| 314202 | 193.1 | GFTFSSYA (SEQ ID NO: 1) | IIGSGGST (SEQ ID NO: 8) | VKDWNTTMITE (SEQ ID NO: 19) |
| 314205 | 102.8 | GFTFSSYA (SEQ ID NO: 1) | ITGSGGTT (SEQ ID NO: 9) | VKDWNTTMITE (SEQ ID NO: 19) |
| 314212 | 125.9 | GFTFSSYA (SEQ ID NO: 1) | LTGNGDST (SEQ ID NO: 10) | VKDWNTTMITE (SEQ ID NO: 19) |
| 314213 | 135.2 | GFTFSSYA (SEQ ID NO: 1) | ITGSGGST (SEQ ID NO: 11) | VKDWNTTMITE (SEQ ID NO: 19) |
| 314219 | 166.9 | GFTFSSYA (SEQ ID NO: 1) | IIGSGGST (SEQ ID NO: 8) | VKDWNTTMITE (SEQ ID NO: 19) |
| 314224 | 175.8 | GFTFSSYA (SEQ ID NO: 1) | IIGSGGST (SEQ ID NO: 8) | VKDWNTTMITE (SEQ ID NO: 19) |
| 314225 | 148.9 | GFTFSSYA (SEQ ID NO: 1) | ITGSGDST (SEQ ID NO: 12) | VKDWNTTMITE (SEQ ID NO: 19) |
| 314228 | 99.1 | GFTFSSYA (SEQ ID NO: 1) | LTGSGDST (SEQ ID NO: 13) | VKDWNTTMITE (SEQ ID NO: 19) |
| 314229 | 124.2 | GFTFSNYA (SEQ ID NO: 3) | ITGDGGST (SEQ ID NO: 7) | VKDWNTTMITE (SEQ ID NO: 19) |
| 314231 | 157.3 | GFTFSRYA (SEQ ID NO: 4) | IVGSGGNT (SEQ ID NO: 14) | VKDWNTTMITE (SEQ ID NO: 19) |
| 314232 | 79.0 | GFTFSSYA (SEQ ID NO: 1) | ITGSGGST (SEQ ID NO: 11) | VKDWNTTMITE (SEQ ID NO: 19) |
| 314235 | 128.3 | GFTFSNYA (SEQ ID NO: 3) | LTGSGGST (SEQ ID NO: 15) | VKDWNTTMITE (SEQ ID NO: 19) |
| 314501 | 251.1 | GFTFTNYA (SEQ ID NO: 2) | IIGSGGST (SEQ ID NO: 8) | VKDWNTTMITE (SEQ ID NO: 19) |
| 314502 | 169.7 | GFTFSSYA (SEQ ID NO: 1) | IIGSGGST (SEQ ID NO: 8) | VKDWNTTMITE (SEQ ID NO: 19) |
| 314503 | 183.3 | GFTFSNYA (SEQ ID NO: 3) | IIGSGGST (SEQ ID NO: 8) | VKDWNTTMITE (SEQ ID NO: 19) |
| 314504 | 176.8 | GFTFSNYA (SEQ ID NO: 3) | IIGSGGST (SEQ ID NO: 8) | VKDWNTTMITE (SEQ ID NO: 19) |
| 314506 | 243.1 | GFTFSNYA (SEQ ID NO: 3) | IIGSGGST (SEQ ID NO: 8) | VKDWNTTMITE (SEQ ID NO: 19) |
| 314508 | 209.0 | GFTFSNYA (SEQ ID NO: 3) | IIGSGATT (SEQ ID NO: 16) | VKDWNTTMITE (SEQ ID NO: 19) |
| 314509 | 241.5 | GFTFSSYA (SEQ ID NO: 1) | IIGSGGST (SEQ ID NO: 8) | VKDWNTTMITE (SEQ ID NO: 19) |
| 314510 | 171.1 | GFTFSSYA (SEQ ID NO: 1) | IIGSGGST (SEQ ID NO: 8) | VKDWNTTMITE (SEQ ID NO: 19) |
| 314512 | 213.8 | GFTFSSYA (SEQ ID NO: 1) | IIGSGGST (SEQ ID NO: 8) | VKDWNTTMITE (SEQ ID NO: 19) |
| 314518 | 182.9 | GFTFSNYA (SEQ ID NO: 3) | IIGSGGTI (SEQ ID NO: 17) | VKDWNTTMITE (SEQ ID NO: 19) |
| 314521 | 234.8 | GFTFSNYA (SEQ ID NO: 3) | IVGGGGTS (SEQ ID NO: 17) | VKDWNTTMITE (SEQ ID NO: 19) |
| 314523 | 195.1 | GFTFSSYA (SEQ ID NO: 1) | ITGDGGST (SEQ ID NO: 7) | VKDWNTTMITE (SEQ ID NO: 19) |
| 314524 | 82.9 | GFTFSNYA (SEQ ID NO: 3) | IVGGGGTS (SEQ ID NO: 18) | VKDWNTTMITE (SEQ ID NO: 19) |
| 314527 | 134.3 | GFTFSSYA (SEQ ID NO: 1) | IIGSGGTI (SEQ ID NO: 11) | VKDWNTTMITE (SEQ ID NO: 19) |
| 314528 | 154.8 | GFTFSNYA (SEQ ID NO: 3) | ITGSGGTS (SEQ ID NO: 17) | VKDWNTTMITE (SEQ ID NO: 19) |
| 314530 | 222.3 | GFTFSNYA (SEQ ID NO: 3) | IVGGGGTS (SEQ ID NO: 17) | VKDWNTTMITE (SEQ ID NO: 19) |
| 314533 | 205.3 | GFTFSNYA (SEQ ID NO: 3) | IIGSGGST (SEQ ID NO: 8) | VKDWNTTMITE (SEQ ID NO: 19) |

| CLONE ID | seq_aa_FR1_FR4 |
|---|---|
| 308607 | EVQLLESGGGLAQPGGSLRLSCAASGFTFSSYAMNWIRQAPGKGLEWVSGISGSGGSTYYADSVKGRFTISRDNSKNTVYLQMNSLRAEDTAVYYCVKDWNTTMITERGQGTLVTVSS (SEQ ID NO: 20) |
| 308915 | EVQLLESGGGLVQPGRSLRLSCAASGFTFNYAMNWVRQAPGKGLEWVSGISGSGGSTYYADSVKGRFTISRDNSKNTLYLQMNSLRAEDTAVYYCVKDWNTTMITERGQGTLVTVSS (SEQ ID NO: 21) |
| 314189 | EVQLLESGGGLVQPGGSLRLSCAASGFTFSSYAMTWVRQAPGKGLEWVSGITENGGSTYYADSVKGRFTISRDNSKNTLDLQMNSLRAEDTAVYYCVKDWNTTMITERGQGTLVTVSS (SEQ ID NO: 22) |
| 314196 | EVQLLESGGGLVQPGGSLRLSCAASGFTFSSYAMSWVRQAPGKGLEWVSGITGDGGSTFYADSVKGRFTISRDNSKNTLYLQMNSLRAEDTAVYYCVKDWNTTMITERGQGTLVTVSS (SEQ ID NO: 23) |
| 314201 | EVQLLESGGGLVQPGGSLRLSCAASGFTFSSYAMSWVRQAPGKGLEWVSGIIGSGGSTYYADSVKGRFTISRDNSKNTLDLQMNSLRAEDTAVYYCVKDWNTTMITERGQGTLVTVSS (SEQ ID NO: 24) |
| 314202 | EVQLLESGGGLVQPGGSLRLSCAASGFTFSSYAMNWVRQAPGKGLEWVSGITGSGGTTYYADSVKGRFTISRDNSKNTLYLQMNSLRAEDTAVYYCVKDWNTTMITERGQGTLVTVSS (SEQ ID NO: 25) |
| 314205 | EVQLLESGGGLVQPGGSLRLSCAASGFTFSSYAMNWVRQAPGKGLEWVSGITGSGGTTYYADSVKGRFTISRDNSKNTVYLQMNSLRAEDTAVYYCVKDWNTTMITERGQGTLVTVSS (SEQ ID NO: 26) |
| 314212 | EVQLLESGGGLVQPGGSLRLSCAASGFTFSSYAMNWVRQAPGKGLEWVSGLTGNGDSTYYADSVKGRFTISRDNSKNTVYLQMNSLRAEDTAVYYCVKDWNTTMITERGQGTLVTVSS (SEQ ID NO: 27) |
| 314213 | EVQLLESGGGLVQPGGSLRLSCAASGFTFSSYAMSWVRQAPGKGLEWVSGITGSGGSTYYADSVKGRFTISRDNSKNTLDLQMNSLRAEDTAVYYCVKDWNTTMITERGQGTLVTVSS (SEQ ID NO: 28) |
| 314219 | EVQLLESGGGLVQPGGSLRLSCAASGFTFSSYAMNWVRQAPGKGLEWVSGIIGSGGSTYYADSVKGRFTISRDNSKNTLYLQMNSLRAEDTAVYYCVKDWNTTMITERGQGTLVTVSS (SEQ ID NO: 29) |
| 314224 | EVQLLESGGGLVQPGGSLRLSCAASGFTFSSYAMNWVRQAPGKGLEWVSGIIGSGGSTYYADSVKGRFTISRDNSKNTVYLQMNSLRAEDTAVYYCVKDWNTTMITERGQGTLVTVSS (SEQ ID NO: 30) |
| 314225 | EVQLLESGGGLVQPGGSLRLSCAASGFTFSSYAMNWVRQAPGKGLEWVSGITGSGGSTYYAASVKGRFSISRDNSQNTLDLQMNSLRAEDTAVYYCVKDWNTTMITERGQGTLVTVSS (SEQ ID NO: 31) |
| 314228 | EVQLLESGGGLVQPGGSLRLSCAASGFTFSSYAMSWVRQAPGKGLEWVSGLTGSGDSTYYADSVKGRFSISRDNSKNTVYLQMNSLRAEDTAVYYCVKDWNTTMITERGQGTLVTVSS (SEQ ID NO: 32) |
| 314229 | EVQLLESGGGLVQPGGSLRLSCAASGFTFSNYAMTWIRQAPGKGLEWVSGITGDGGSTFYADSVKGRFSISRDNSKNTLDLQMNSLRAEDTAVYYCVKDWNTTMITERGQGTLVTVSS (SEQ ID NO: 33) |
| 314231 | EVQLLESGGGLVQPGGSLRLSCAASGFTFSRYAMNWVRQAPGKGLEWVSGIVGSGGNTYYADSVKGRFSISRDNSKNTLYLQMNSLRAEDTAVYYCVKDWNTTMITERGQGTLVTVSS (SEQ ID NO: 34) |
| 314232 | EVQLLESGGGLVQPGGSLRLSCAASGFTFSSYAMSWVRQAPGKGLEWVSGITGSGGSTYYADSVKGRFSISRDNSKNTLDLQMNSLRAEDTAVYYCVKDWNTTMITERGQGTLVTVSS (SEQ ID NO: 35) |
| 314235 | EVQLLESGGGLVQPGGSLRLSCAASGFTFSNYAMNWVRQAPGNGLEWVSGLTGSGGTYYADSVKGRFTISRDNSKNTVYLQMNSLRAEDTAVYYCVKDWNTTMITERGQGTLVTVSS (SEQ ID NO: 36) |

Fig 2 (CONT.)

| ID | Sequence |
|---|---|
| 314501 | EVQLLESGGGLVQPGGSLRLSCAASGFTFTNYAMNWVRQAPGKGLEWVSGIIGSGGSTYYADSVKGRFTISRDNSKNTLYLQMNSLRA EDTAVYYCVKDWNTTMITERGQGTLVTVSS (SEQ ID NO: 37) |
| 314502 | EVQLLESGGGVVQPGRSLRLSCAASGFTFSSYAMSWVRQAPGKGLEWVSGIIGSGGSTYYADSVKGRFTISRDNSKNTLYLQMNSLRA EDTAVYYCVKDWNTTMITERGQGTLVTVSS (SEQ ID NO: 38) |
| 314503 | EVQLLESGGGLVQPGGSLRLSCAASGFTFSNYAMSWVRQAPGKGLEWVSGIIGSGGSTYYADSVKGRFSISRDNSKNTLYLQMNSLRA EDTAVYYCVKDWNTTMITERGQGTLVTVSS (SEQ ID NO: 39) |
| 314504 | EVQLLESGGGLVQPGGSLRLSCAASGFTFSSYAMSWVRQAPGKGLEWVSGIIGSGGSTYYADSVKGRFTISRDNSKNTLYLQMNSLRV EDTAVYYCVKDWNTTMITERGQGTLVTVSS (SEQ ID NO: 40) |
| 314506 | EVQLLESGGGVVQPGRSLRLSCAASGFTFSNYAMNWVRQAPGKGLEWVSGIIGSGGSTYYADSVKGRFTISRDNSKNTLYLQMNSLRA EDTAVYYCVKDWNTTMITERGQGTLVTVSS (SEQ ID NO: 41) |
| 314508 | EVQLLESGGGLVQPGGSLRLSCAASGFTFSNYAMNWVRQAPGKGLEWVSGIIGSGGSTYYADSVKGRFTISRDNSKNTLYLQMNSLRA EDTAVYYCVKDWNTTMITERGQGTLVTVSS (SEQ ID NO: 42) |
| 314509 | EVQLLESGGGLVQPGGSLTLSCAASGFTFSNYAMNWVRQAPGKGLEWVSGIIGSGATTYYADSVKGRFTISRDNSKNTLNLQMNSLRA EDTAIYYCVKDWNTTMITERGQGTLVTVSS (SEQ ID NO: 43) |
| 314510 | EVQLLESGGGLVQPGGSLRLSCAASGFTFSNYAMNWVRQAPGKGLEWVSGIIGSGGSTYYADSVKGRFTISRDNSKNTLYLQMNSLRA EDTAVYYCVKDWNTTMITERGQGTLVTVSS (SEQ ID NO: 44) |
| 314512 | EVQLLESGGGVVQPGRSLRLSCAASGFTFSSYAMSWVRQAPGKGLEWVSGIIGSGGSTYYADSVKGRFTISRDNSKNTLYLQMNSLRA EDTAVYYCVKDWNTTMITERGQGTLVTVSS (SEQ ID NO: 45) |
| 314518 | EVQLLESGGGLVQPGGSLRLSCAASGFTFSSYAMSWVRQAPGKGLEWVSGIIGSGGSTFYADSVKGRFTISRDNSKNTLYLQMNSLRA EDTAVYYCVKDWNTTMITERGQGTLVTVSS (SEQ ID NO: 46) |
| 314521 | EVQLLESGGGLVQPGESLRLSCAASGFTFSNYAMTWIRQAPGKGLEWVSGITGDGGSTFYADSVKGRFTISRDNSKNTLYLQMNSLRA EDTAVYYCVKDWNTTMITERGQGTLVTVSS (SEQ ID NO: 47) |
| 314523 | EVQLLESGGGLVQPGGSLRLSCAASGFTFSNYAMTWIRQAPGKGLEWVSGIVGGGGTSYYADSVKGRFTISRDNSKNTLYLQMNSLRA EDTAVYYCVKDWNTTMITERGQGTLVTVSS (SEQ ID NO: 48) |
| 314524 | EVQLLESGGGLVQPGGSLRLSCAASGFTFSSYAMTWIRQAPGKGLEWVSGIVGGGGTSYYADSVKGRFTISRDNSKNTLYLQMNSLRA EDTAVYYCVKDWNTTMITERGQGTLVTVSS (SEQ ID NO: 49) |
| 314527 | EVQLLESGGGLVQPGGSLRLSCAASGFTFSSYAMSWVRQAPGKGLEWVSGIIGSGGITYYADSVKGRFTISRDNSKNTLNLQMNSLRA EDTAVYYCVKDWNTTMITERGQGTLVTVSS (SEQ ID NO: 50) |
| 314528 | EVQLLESGGGLVQPGGSLRLSCAASGFTFSNYAMNWVRQAPGKGLEWVSGITGSGGSTYYADSVKGRFTISRDNSKNTLYLQMNSLRV EDTAVYYCVKDWNTTMITERGQGTLVTVSS (SEQ ID NO: 51) |
| 314530 | EVQLLESGGGLVQPGGSLRLSCAASGFTFSSYAMNWVRQAPGKGLEWVSGIVGGGGTSYYADSVKGRFTISRDNSKNTLYLQMNSLRA EDTAVYYCVKDWNTTMITERGQGTLVTVSS (SEQ ID NO: 52) |
| 314533 | EVQLLESGGGLVQPGGSLRLSCAASGFTFSSYAMNWVRQAPGKGLEWVSGIIGSGGSTYYADSVKGRFTISRDNSKNTLYLQMNSLRV EDTAVYYCVKDWNTTMITERGQGTLVTVSS (SEQ ID NO: 53) |

FIG. 3

| CLONE ID | MFI/bkgrd (H929 cell bind) | MFI/bkgrd (RPMI8226 cell bind) | % APRIL binding | ELISA hBCMA/bkgrd | ELISA IgG1k/bkgrd | ELISA BYP score |
|---|---|---|---|---|---|---|
| 308607 | | | | | | |
| 308915 | | | | | | |
| 314189 | 123.5 | not measured | not measured | not measured | not measured | not measured |
| 314196 | 133.6 | not measured | not measured | not measured | not measured | not measured |
| 314201 | | not measured | not measured | not measured | not measured | not measured |
| 314202 | | not measured | not measured | not measured | not measured | not measured |
| 314205 | 102.8 | not measured | not measured | not measured | not measured | not measured |
| 314212 | 125.9 | not measured | not measured | not measured | not measured | not measured |
| 314213 | 135.2 | not measured | not measured | not measured | not measured | not measured |
| 314219 | | not measured | not measured | not measured | not measured | not measured |
| 314224 | | not measured | not measured | not measured | not measured | not measured |
| 314225 | 148.9 | not measured | not measured | not measured | not measured | not measured |
| 314228 | 89.1 | not measured | not measured | not measured | not measured | not measured |
| 314229 | 124.2 | not measured | not measured | not measured | not measured | not measured |
| 314231 | 157.3 | not measured | not measured | not measured | not measured | not measured |
| 314232 | | not measured | not measured | not measured | not measured | not measured |
| 314235 | 128.3 | not measured | not measured | not measured | not measured | not measured |
| 314501 | | not measured | not measured | not measured | not measured | not measured |
| 314502 | | not measured | not measured | not measured | not measured | not measured |
| 314503 | | not measured | not measured | not measured | not measured | not measured |
| 314504 | | not measured | not measured | not measured | not measured | not measured |
| 314506 | | not measured | not measured | not measured | not measured | not measured |
| 314508 | | not measured | not measured | not measured | not measured | not measured |
| 314509 | | not measured | not measured | not measured | not measured | not measured |
| 314510 | | not measured | not measured | not measured | not measured | not measured |
| 314512 | | not measured | not measured | not measured | not measured | not measured |
| 314518 | | not measured | not measured | not measured | not measured | not measured |
| 314521 | | not measured | not measured | not measured | not measured | not measured |
| 314523 | | not measured | not measured | not measured | not measured | not measured |
| 314524 | | not measured | not measured | not measured | not measured | not measured |
| 314527 | 134.3 | not measured | not measured | not measured | not measured | not measured |
| 314528 | 154.8 | not measured | not measured | not measured | not measured | not measured |
| 314530 | | not measured | not measured | not measured | not measured | not measured |
| 314533 | | not measured | not measured | not measured | not measured | not measured |

FIG. 4

| huBCMA-Fc | CyBCMA | huBCMA e coli frag | huBCMA full wht germ | hu IgG1kappa | H.S.A | Animal |
|---|---|---|---|---|---|---|
| 325 | 296 | 501 | 245 | | | r12431 (HC27) |
| 281 | | 417 | 247 | | | r12455 (HC27) |
| 262 | 267 | 418 | 245 | 303 | | r12514 (HC27) |
| 314 | | 519 | 444 | | | r12271 (HC28) |
| 260 | 290 | 421 | 413 | 296 | | r12276 (HC28) |
| 594 | 476 | | | | | r12278 (HC28) |
| | | | | | | r12516 (HC27) |
| | | | | | | goat anti huBCMA |

DAY 35 SERUM - ELISA TESTING (testing from 6/12 animals)
Assayed 1:500 dilution of d35 serum
Signal/H.S.A, adjusted for each animal FIG. 6
A) scFv CAR-T construct
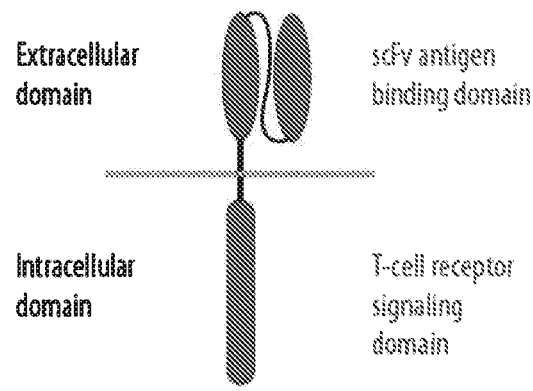
B) human VH CAR-T construct
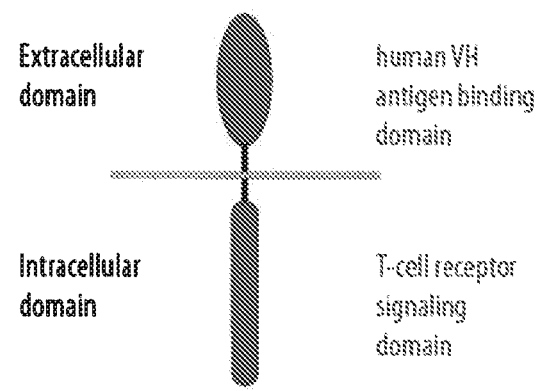

SEQUENCE LISTING

```
<160> NUMBER OF SEQ ID NOS: 56

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Phe Thr Phe Ser Ser Tyr Ala
1               5

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Phe Thr Phe Thr Asn Tyr Ala
1               5

<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Phe Thr Phe Ser Asn Tyr Ala
1               5

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Phe Thr Phe Ser Arg Tyr Ala
1               5

<210> SEQ ID NO 5
<211> LENGTH: 8
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ile Ser Gly Ser Gly Gly Ser Thr
1               5

<210> SEQ ID NO 6
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ile Thr Glu Asn Gly Gly Ser Thr
1               5

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Ile Thr Gly Asp Gly Gly Ser Thr
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ile Ile Gly Ser Gly Gly Ser Thr
1               5

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ile Thr Gly Ser Gly Gly Thr Thr
1               5

<210> SEQ ID NO 10
<211> LENGTH: 8
<212> TYPE: PRT
<213> ORGANISM: Artificial Sequence
<220> FEATURE:
<221> NAME/KEY: source
```

-continued

<223> OTHER INFORMATION: /note="Description of Artificial Sequence:
     Synthetic peptide"

<400> SEQUENCE: 10

Leu Thr Gly Asn Gly Asp Ser Thr
1               5

<210> SEQ ID NO 11
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 11

Ile Thr Gly Ser Gly Gly Ser Thr
1               5

<210> SEQ ID NO 12
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 12

Ile Thr Gly Ser Gly Asp Ser Thr
1               5

<210> SEQ ID NO 13
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 13

Leu Thr Gly Ser Gly Asp Ser Thr
1               5

<210> SEQ ID NO 14
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 14

Ile Val Gly Ser Gly Gly Asn Thr
1               5

<210> SEQ ID NO 15
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 15

```
Leu Thr Gly Ser Gly Gly Ser Thr
1               5

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ile Ile Gly Ser Gly Ala Thr Thr
1               5

<210> SEQ ID NO 17
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ile Val Gly Gly Gly Gly Thr Ser
1               5

<210> SEQ ID NO 18
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ile Ile Gly Ser Gly Gly Thr Thr
1               5

<210> SEQ ID NO 19
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Val Lys Asp Trp Asn Thr Thr Met Ile Thr Glu
1               5                   10

<210> SEQ ID NO 20
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Glu Val Gln Leu Leu Glu Ser Gly Gly Gly Leu Ala Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Asn Trp Ile Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 21
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Thr Asn Tyr
            20                  25                  30

Ala Met Asn Trp Val Arg Gln Ala Pro Gly Lys Gly Leu Glu Trp Val
        35                  40                  45

Ser Gly Ile Ser Gly Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 22
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Gly Ile Thr Glu Asn Gly Gly Ser Thr Tyr Tyr Ala Asp Ser Val
```

```
                    50                  55                  60
Lys Gly Arg Phe Thr Ile Ser Arg Asp Asn Ser Lys Asn Thr Leu Asp
 65                  70                  75                  80

Leu Gln Met Asn Ser Leu Arg Ala Glu Asp Thr Ala Val Tyr Tyr Cys
                 85                  90                  95

Val Lys Asp Trp Asn Thr Thr Met Ile Thr Glu Arg Gly Gln Gly Thr
                100                 105                 110

Leu Val Thr Val Ser Ser
            115

<210> SEQ ID NO 23
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Gly Ile Thr Gly Asp Gly Gly Ser Thr Phe Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Lys Asp Trp Asn Thr Thr Met Ile Thr Glu Arg Gly Gln Gly Thr
                100                 105                 110

Leu Val Thr Val Ser Ser
            115

<210> SEQ ID NO 24
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Gly Ile Ile Gly Ser Gly Ser Thr Tyr Tyr Ala Asp Ser Val
         50                  55                  60

Lys Gly Arg Phe Ser Ile Ser Arg Asp Asn Ser Lys Asn Thr Leu Asp
 65                  70                  75                  80

Leu Gln Met Asn Ser Leu Arg Ala Glu Asp Thr Ala Val Tyr Tyr Cys
                 85                  90                  95
```

```
Val Lys Asp Trp Asn Thr Thr Met Ile Thr Glu Arg Gly Gln Gly Thr
            100                 105                 110

Leu Val Thr Val Ser Ser
        115

<210> SEQ ID NO 25
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ile Thr Gly Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 26
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ile Thr Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Val Lys Asp Trp Asn Thr Thr Met Ile Thr Glu Arg Gly Gln Gly Thr
            100                 105                 110

Leu Val Thr Val Ser Ser
        115
```

<210> SEQ ID NO 27
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Leu Thr Gly Asn Gly Asp Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 28
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ile Thr Gly Ser Gly Ser Thr Tyr Tyr Ala Asp Ser Val
    50                  55                  60

Lys Gly Arg Phe Ser Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 29
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ile Ile Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 30
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ile Ile Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 31
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 31

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ile Thr Gly Ser Gly Asp Ser Thr Tyr Tyr Ala Ala Ser Val
50                  55                  60

Lys Gly Arg Phe Ser Ile Ser Arg Asp Asn Ser Gln Asn Thr Leu Asp
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115
```

<210> SEQ ID NO 32
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 32

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Leu Thr Gly Ser Gly Asp Ser Thr Tyr Tyr Ala Asp Ser Val
50                  55                  60

Lys Gly Arg Phe Thr Ile Ser Arg Asp Asn Asp Lys Asn Thr Val Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115
```

<210> SEQ ID NO 33
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 33

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Ile Arg Gln Ala Pro Gly Lys Gly Leu Glu Trp Val
        35                  40                  45
```

Ser Gly Ile Thr Gly Asp Gly Gly Ser Thr Phe Tyr Ala Asp Ser Val
    50                  55                  60

Lys Gly Arg Phe Ser Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
            115

<210> SEQ ID NO 34
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
                20                  25                  30

Ala Met Asn Trp Ile Arg Gln Ala Pro Gly Lys Gly Leu Glu Trp Val
            35                  40                  45

Ser Gly Ile Val Gly Ser Gly Asn Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
            115

<210> SEQ ID NO 35
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Gly Ile Thr Gly Ser Gly Ser Thr Tyr Tyr Ala Asp Ser Val
    50                  55                  60

Lys Gly Arg Phe Ser Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys

```
                    85                  90                  95
Val Lys Asp Trp Asn Thr Thr Met Ile Thr Glu Arg Gly Gln Gly Thr
                100                 105                 110

Leu Val Thr Val Ser Ser
        115

<210> SEQ ID NO 36
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Asn Gly Leu Glu Trp Val
        35                  40                  45

Ser Gly Leu Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
                100                 105                 110

Leu Val Thr Val Ser Ser
        115

<210> SEQ ID NO 37
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ala Met Asn Trp Val Arg Gln Ala Pro Gly Lys Gly Leu Glu Trp Val
        35                  40                  45

Ser Gly Ile Ile Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
                100                 105                 110

Leu Val Thr Val Ser Ser
        115
```

<210> SEQ ID NO 38
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

```
Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ile Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115
```

<210> SEQ ID NO 39
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ile Gly Ser Gly Gly Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115
```

<210> SEQ ID NO 40
<211> LENGTH: 118
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ile Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 41
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Gly Ile Ile Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 42
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Glu Val Gln Leu Leu Glu Ser Gly Gly Gly Leu Val Gln Pro Gly Gly
```

```
                1               5                  10                 15
Ser Leu Arg Leu Ser Cys Ala Ala Ser Gly Phe Thr Phe Ser Asn Tyr
            20                  25                 30

Ala Met Asn Trp Val Arg Gln Ala Pro Gly Lys Gly Leu Glu Trp Val
        35                  40                  45

Ser Gly Ile Ile Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
            115

<210> SEQ ID NO 43
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Glu Val Gln Leu Leu Glu Ser Gly Gly Gly Leu Val Gln Pro Gly Gly
1               5                   10                  15

Ser Leu Thr Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Gly Ile Ile Gly Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Ile Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
            115

<210> SEQ ID NO 44
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45
```

Ser Gly Ile Ile Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
            115

<210> SEQ ID NO 45
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Gly Ile Ile Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
            115

<210> SEQ ID NO 46
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Gly Ile Ile Gly Ser Gly Gly Ser Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 47
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Glu Val Gln Leu Leu Glu Ser Gly Gly Gly Leu Val Gln Pro Gly Glu
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Gly Ile Val Gly Gly Gly Thr Ser Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 48
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Ile Arg Gln Ala Pro Gly Lys Gly Leu Glu Trp Val
        35                  40                  45

Ser Gly Ile Thr Gly Asp Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser

<210> SEQ ID NO 49
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Ile Arg Gln Ala Pro Gly Lys Gly Leu Glu Trp Val
        35                  40                  45

Ser Gly Ile Val Gly Gly Gly Thr Ser Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 50
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ile Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Ile Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 51
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Gly Ile Thr Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 52
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Gly Ile Val Gly Gly Gly Thr Ser Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115

<210> SEQ ID NO 53
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Gly Ile Ile Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115
```

```
<210> SEQ ID NO 54
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ile Ser Gly Gly Gly Gly Ser Thr
1               5
```

```
<210> SEQ ID NO 55
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Thr"
<220> FEATURE:
<221> NAME/KEY: VARIANT
<222> LOCATION: (6)..(6)
<223> OTHER INFORMATION: /replace="Asn" or "Arg"
<220> FEATURE:
<221> NAME/KEY: MISC_FEATURE
<222> LOCATION: (1)..(8)
<223> OTHER INFORMATION: /note="Variant residues given in the sequence
      have no preference with respect to those in the annotations
      for variant positions"

<400> SEQUENCE: 55

Gly Phe Thr Phe Ser Ser Tyr Ala
1               5
```

```
<210> SEQ ID NO 56
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
```

```
<222> LOCATION: (1)..(1)
<223> OTHER INFORMATION: /replace="Leu"
<220> FEATURE:
<221> NAME/KEY: VARIANT
<222> LOCATION: (2)..(2)
<223> OTHER INFORMATION: /replace="Thr" or "Ile" or "Val"
<220> FEATURE:
<221> NAME/KEY: VARIANT
<222> LOCATION: (3)..(3)
<223> OTHER INFORMATION: /replace="Glu"
<220> FEATURE:
<221> NAME/KEY: VARIANT
<222> LOCATION: (4)..(4)
<223> OTHER INFORMATION: /replace="Gly" or "Asn" or "Asp"
<220> FEATURE:
<221> NAME/KEY: VARIANT
<222> LOCATION: (6)..(6)
<223> OTHER INFORMATION: /replace="Asp" or "Ala"
<220> FEATURE:
<221> NAME/KEY: VARIANT
<222> LOCATION: (7)..(7)
<223> OTHER INFORMATION: /replace="Thr" or "Asn"
<220> FEATURE:
<221> NAME/KEY: VARIANT
<222> LOCATION: (8)..(8)
<223> OTHER INFORMATION: /replace="Ser"
<220> FEATURE:
<221> NAME/KEY: MISC_FEATURE
<222> LOCATION: (1)..(8)
<223> OTHER INFORMATION: /note="Variant residues given in the sequence
      have no preference with respect to those in the annotations
      for variant positions"

<400> SEQUENCE: 56

Ile Ser Gly Ser Gly Gly Ser Thr
1               5
```

ANTI-BCMA HEAVY CHAIN-ONLY ANTIBODIES

CROSS REFERENCE TO RELATED APPLICATIONS

This application claims priority benefit of the filing date of U.S. Provisional Patent Application Ser. No. 62/437,588, filed on Dec. 21, 2016, the disclosure of which application is herein incorporated by reference in its entirety.

SEQUENCE LISTING

The instant application contains a Sequence Listing which has been submitted electronically in ASCII format and is hereby incorporated by reference in its entirety. Said ASCII copy, created on Jan. 17, 2018, is named TNO-0002-US_SL.txt and is 46 KB in size.

FIELD OF THE INVENTION

The present invention concerns anti-BCMA heavy chain-only antibodies (HCAb). The invention further concerns methods of making such antibodies, compositions, including pharmaceutical compositions, comprising such antibodies, and their use to treat a B-cell disorder characterized by the expression of BCMA.

BACKGROUND OF THE INVENTION

B-Cell Maturation Antigen (BCMA)

BCMA, also known as tumor necrosis factor superfamily member 17 (TNFRSF17) (UniProt Q02223), is a cell surface receptor exclusively expressed on plasma cells and plasmablasts. BCMA is a receptor for two ligands in the tumor necrosis factor (TNF) superfamily: APRIL (a proliferation-inducing ligand, also known as TNFSF13; TALL-2 and TRDL-1; the high affinity ligand for BCMA) and B cell activation factor (BAFF) (also known as BLyS; TALL-1; THANK; zTNF4; TNFSF20; and D8Ertd387e; the low affinity ligand for BCMA). APRIL and BAFF are growth factors that bind BCMA and promote survival of plasma cells. BCMA is also highly expressed on malignant plasma cells in human multiple myeloma (MM). Antibodies binding to BCMA are described, for example, in Gras et al., 1995, Int. Immunol. 7:1093-1106, WO200124811 and WO200124812. Anti-BCMA antibodies that cross-react with TACI are described in WO2002/066516. Bispecific antibodies against BCMA and CD3 are described, for example, in US 2013/0156769 A1 and US 2015/0376287 A1. An anti-BCMA antibody-MMAE or -MMAF conjugate has been reported to selectively induce killing of multiple myeloma cells (Tai et al., Blood 2014, 123(20): 3128-38). Ali et al., Blood 2016, 128(13):1688-700, have reported that in a clinical trial (#NCT02215967) chimeric antigen receptor (CAR) T cells targeting BCMA resulted in remission of multiple myeloma in human patients.

Heavy Chain-Only Antibodies

In a conventional IgG antibody, the association of the heavy chain and light chain is due in part to a hydrophobic interaction between the light chain constant region and the CH1 constant domain of the heavy chain. There are additional residues in the heavy chain framework 2 (FR2) and framework 4 (FR4) regions that also contribute to this hydrophobic interaction between the heavy and light chains. It is known, however, that sera of camelids (sub-order Tylopoda which includes camels, dromedaries and llamas) contain a major type of antibodies composed solely of paired H-chains (heavy-chain only antibodies or HCAbs). The HCAbs of *Carnelidae* (*Camelus dromedarius, Camelus bactrianus, Lama glama, Lama guanaco, Lama alpaca* and *Lama vicugna*) have a unique structure consisting of a single variable domain (VHH), a hinge region and two constant domains (CH2 and CH3), which are highly homologous to the CH2 and CH3 domains of classical antibodies. These HCAbs lack the first domain of the constant region (CH1) which is present in the genome, but is spliced out during mRNA processing. The absence of the CH1 domain explains the absence of the light chain in the HCAbs, since this domain is the anchoring place for the constant domain of the light chain. Such HCAbs naturally evolved to confer antigen-binding specificity and high affinity by three CDRs from conventional antibodies or fragments thereof (Muyldermans, 2001; *J Biotechnol* 74:277-302; Revets et al., 2005; *Expert Opin Biol Ther* 5:111-124). Cartilaginous fish, such as sharks, have also evolved a distinctive type of immunoglobulin, designated as IgNAR, which lacks the light polypeptide chains and is composed entirely by heavy chains. IgNAR molecules can be manipulated by molecular engineering to produce the variable domain of a single heavy chain polypeptide (vNARs) (Nuttall et al. *Eur. J. Biochem.* 270, 3543-3554 (2003); Nuttall et al. *Function and Bioinformatics* 55, 187-197 (2004); Dooley et al., *Molecular Immunology* 40, 25-33 (2003)).

The ability of heavy chain-only antibodies devoid of light chain to bind antigen was established in the 1960s (Jaton et al. (1968) *Biochemistry,* 7, 4185-4195). Heavy chain immunoglobulin physically separated from light chain retained 80% of antigen-binding activity relative to the tetrameric antibody. Sitia et al. (1990) *Cell,* 60, 781-790 demonstrated that removal of the CH1 domain from a rearranged mouse μ gene results in the production of a heavy chain-only antibody, devoid of light chain, in mammalian cell culture. The antibodies produced retained VH binding specificity and effector functions.

Heavy chain antibodies with a high specificity and affinity can be generated against a variety of antigens through immunization (van der Linden, R. H., et al. *Biochim. Biophys. Acta.* 1431, 37-46 (1999)) and the VHH portion can be readily cloned and expressed in yeast (Frenken, L. G. J., et al. *J. Biotechnol.* 78, 11-21 (2000)). Their levels of expression, solubility and stability are significantly higher than those of classical F(ab) or Fv fragments (Ghahroudi, M. A. et al. *FEBS Lett.* 414, 521-526 (1997)).

Mice in which the λ (lambda) light (L) chain locus and/or the λ and κ (kappa) L chain loci have been functionally silenced and antibodies produced by such mice are described in U.S. Pat. Nos. 7,541,513 and 8,367,888. Recombinant production of heavy chain-only antibodies in mice and rats has been reported, for example, in WO2006008548; U.S. Application Publication No. 20100122358; Nguyen et al., 2003, *Immunology;* 109(1), 93-101; Brüggemann et al., *Crit. Rev. Immunol.;* 2006, 26(5):377-90; and Zou et al., 2007, *J Exp Med;* 204(13): 3271-3283. The production of knockout rats via embryo microinjections of zinc-finger nucleases is described in Geurts et al., 2009, *Science,* 325(5939):433. Soluble heavy chain-only antibodies and transgenic rodents comprising a heterologous heavy chain locus producing such antibodies are described in U.S. Pat. Nos. 8,883,150 and 9,365,655. CAR-T structures comprising single-domain antibodies as binding (targeting) domain are described, for example, in Iri-Sofia et al., 2011, *Experimental Cell Research* 317:2630-2641 and Jamnani et al., 2014, *Biochim Biophys Acta,* 1840:378-386.

SUMMARY OF THE INVENTION

The present invention concerns anti-BCMA antibodies.

In one aspect, the invention concerns a heavy chain-only antibody binding to human B-Cell Maturation Antigen (BCMA) comprising a heavy chain variable region comprising:
(a) a CDR1 having at least 95% sequence identity to any of the sequences of SEQ ID NOs: 1 to 4; and/or
(b) a CDR2 having at least 95% sequence identity to any of the sequences of SEQ ID NOs: 5 to 18; and/or
(c) a CDR3 having at least 95% sequence identity to SEQ ID NO: 19.

In one embodiment, the CDR1, CDR2, and CDR3 sequences are present in a human framework.

In another embodiment, the anti-BCMA heavy chain-only antibody further comprises a heavy chain constant region sequence in the absence of a CH1 sequence.

In yet another embodiment, the heavy chain-only antibody comprises:
(a) a sequence selected from the group consisting of SEQ ID NOs: 1 to 4; and/or
(b) a CDR2 sequence selected from the group consisting of SEQ ID NOs: 5 to 18; and/or
(c) a CDR3 of SEQ ID NO: 19.

In a further embodiment, the anti-BCMA heavy chain-only antibody comprises:
(a) a CDR1 sequence selected from the group consisting of SEQ ID NOs: 1 to 4; and
(b) a CDR2 sequence selected from the group consisting of SEQ ID N Os: 5 to 18; and
(c) a CDR3 of SEQ ID NO: 19.

In a still further embodiment, the heavy chain-only anti-BCMA antibody comprises a heavy chain variable region having at least 95% sequence identity to any of the sequences of SEQ ID NOs: 20 to 53.

In another embodiment, the heavy chain-only anti-BCMA antibody comprises a heavy chain variable region sequence selected from the group consisting of SEQ ID NOs: 20 to 53.

In another aspect, the invention concerns a heavy chain-only antibody binding to human B-Cell Maturation Antigen (BCMA) comprising a heavy chain variable region comprising a heavy chain variable comprising
(a) a CDR1 sequence of the formula:

G F T F X1 X2 Y A (SEQ ID NO: 55)

where
X1 is S or T; and
X2 is S, N or R; and
(b) CDR2 sequence of the formula:

X3 X4 X5 X6 G X7 X8 X9 (SEQ ID NO: 56)

where
X3 is I or L;
X4 is S, T, I or V;
X5 is G or E;
X6 is S, G, N or D;
X7 is G, D or A;
X8 is S, T or N;
X9 is T or S, and
(c) a CDR3 sequence of SEQ ID NO: 19
in a human VH framework.

In a further aspect, the invention concerns a heavy chain-only antibody binding to human B-Cell Maturation Antigen (BCMA) comprising a heavy chain variable region comprising CDR1, CDR2 and CDR3 sequences in a human VH framework wherein the CDR sequences are a sequence with at least 95% identity to a CDR sequence selected from the group consisting of SEQ ID NOs:1-19.

In one embodiment, such antibody comprises a heavy chain variable region comprising CDR1, CDR2 and CDR3 sequences in a human VH framework wherein the CDR sequences are selected from the group consisting of SEQ ID NOs:1-19.

In a further aspect, the invention concerns a heavy chain-only antibody binding to human B-Cell Maturation Antigen (BCMA) comprising a heavy chain variable region comprising
(a) a CDR1 of SEQ ID NO: 1, a CDR2 of SEQ ID NO: 5; and a CDR3 of SEQ ID NO: 19; or
(b) a CDR1 of SEQ ID NO: 2, a CDR2 of SEQ ID NO: 5; and a CDR3 of SEQ ID NO: 19 in a human VH framework.

In one embodiment, the heavy chain-only antibody is multi-specific, such as bispecific.

In another embodiment, the heavy chain-only antibody has binding affinity to two different BCMA proteins.

In yet another embodiment, the heavy chain-only antibody has binding affinity to two different epitopes on the same BCMA protein.

In a further embodiment, the heavy chain-only antibody has binding affinity to an effector cell.

In a still further embodiment, the heavy chain-only antibody has binding affinity to a T-cell antigen.

In another embodiment, the heavy chain-only antibody has binding affinity to CD3.

In a different aspect, the heavy chain-only antibody hereinabove described is in a CAR-T format.

In a further aspect, the invention concerns a pharmaceutical composition comprising an anti-BCMA heavy chain-only antibody herein.

In a still further aspect, the invention concerns a method for the treatment of a B-cell disorder characterized by the expression of BCMA comprising administering to a subject with such disorder an anti-BCMA heavy chain-only antibody herein, or a pharmaceutical composition comprising such antibody.

In various embodiments, the B-cell disorder may, for example, be multiple myeloma or systemic lupus erythematosus.

In a further aspect, the invention concerns a polynucleotide encoding an anti-BCMA heavy chain-only antibody herein.

In a still further aspect, the invention concerns a vector comprising a polynucleotide encoding an anti-BCMA heavy chain-only antibody herein.

In another aspect, the invention concerns a cell comprising a polynucleotide encoding an anti-BCMA heavy chain-only antibody herein, or a vector comprising such polynucleotide.

In yet another aspect, the invention concerns a method of producing an antibody herein, comprising growing a cell as hereinabove described under conditions permissive for expression of the antibody, and isolating the antibody from the cells.

In a further aspect, the invention concerns a method of making an anti-BCMA heavy chain-only antibody as described herein, comprising immunizing a UniRat animal with BCMA and identifying BCMA-binding heavy chain sequences.

These and further aspects will be further explained in the rest of the disclosure, including the Examples.

BRIEF DESCRIPTION OF THE DRAWINGS

FIG. 1 shows the CDR1, CDR2 and CDR3 amino acid sequences of 34 heavy chain-only anti-BCMA antibodies of the invention.

FIG. 2 shows the heavy chain variable region sequences of 34 heavy chain-only anti-BCMA antibodies of the invention.

FIG. 3: Heatmap summary of the antibody binding activities of 34 heavy chain-only anti-BCMA antibodies expressed in HEK 293 cells. Red indicates strong binding while blue represents weak or negative binding results. Cell binding assays were run on all 34 antibodies and were shown to bind H929 cells. Two antibodies encoding either VH sequence 308607 or VH sequence 308915 were tested for binding to an untagged human BCMA ECD fragment, and two off-target protein controls including human IgG1 and a baculovirus protein extract (BVP), and BCMA+MM cell line RPMI8226. Two UniAbs were also evaluated for the ability to block APRIL (ligand)/BCMA (receptor) binding in a recombinant protein ELISA-style assay.

FIG. 4: Serum binding activity against the immunogen and other on- and off-target proteins. A single 1:500 dilution of d35 serum from a subset of the animals was assayed for binding activity to a series of proteins in a standard ELISA assay. On-target proteins include human BCMA Fc region (huBCMA-Fc), a cyno BCMA ECD fused to a human Fc sequence (cyBCMA), and huBCMA from two other sources that do not have the Fc fusion (*E. coli* and wheat germ). Human serum albumin and human IgG1 were used to assess off-target reactivity.

FIG. 6: Representative CAR-T constructs comprising a human VH extracellular binding domain.

DETAILED DESCRIPTION OF THE PREFERRED EMBODIMENTS

Figure 5:
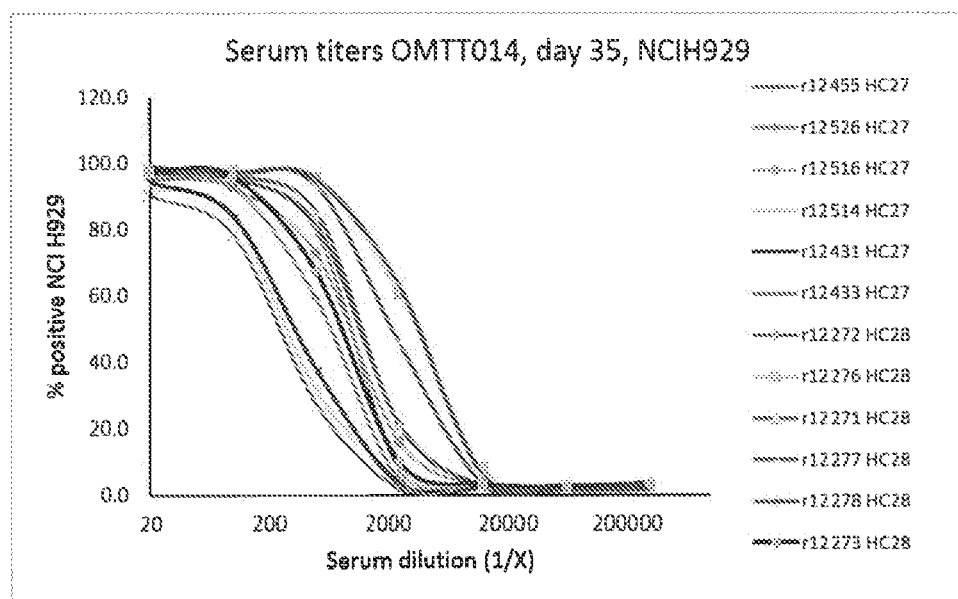
FIG. 5: Serum binding activity against a BCMA+ cell line (NCI-H929). Titers were evaluated by testing for serum binding to NCI-H929 cells by flow cytometry using a PE-conjugated anti-rat IgG2a antibody. Percent of NCI-H929 cells showing significant staining was assessed.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless indicated otherwise, antibody residues herein are numbered according to the Kabat numbering system (e.g., Kabat et al., Sequences of Immunological Interest. 5th Ed. Public Health Service, National Institutes of Health, Bethesda, Md. (1991)).

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All references cited throughout the disclosure, including patent applications and publications, are incorporated by reference herein in their entirety.

I. Definitions

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The terms "heavy chain-only antibody," "heavy-chain antibody" and "HCAb" are used interchangeably, and refer, in the broadest sense, to antibodies lacking the light chain of a conventional antibody. Since the homodimeric HCAbs lack a light chain and thus a VL domain, the antigen is recognized by one single domain, i.e., the variable domain of the heavy chain of a heavy-chain antibody (VH). The term specifically includes, without limitation, homodimeric antibodies comprising the VH antigen-binding domain and the CH2 and CH3 constant domains, in the absence of the CH1 domain; functional (antigen-binding) variants of such antibodies, soluble VH variants, Tg-NAR comprising a homodimer of one variable domain (V-NAR) and five C-like constant domains (C-NAR) and functional fragments thereof; and soluble single domain antibodies (sdAbs). In one embodiment, the heavy chain-only antibody is composed of the variable region antigen-binding domain composed of framework 1, CDR1, framework 2, CDR2, framework 3, CDR3, and framework 4. In one embodiment, the heavy chain-only antibody is composed of an antigen-binding domain, at least part of a hinge region and CH2 and CH3 domains. In another embodiment, the heavy chain-only antibody is composed of an antigen-binding domain, at least part of a hinge region and a CH2 domain. In a further embodiment, the heavy chain-only antibody is composed of an antigen-binding domain, at least part of a hinge region and a CH3 domain. Heavy chain-only antibodies in which the CH2 and/or CH3 domain is truncated are also included herein. In a further embodiment the heavy chain is composed of an antigen binding domain, and at least one CH (CH1, CH2, CH3, or CH4) domain but no hinge region. The heavy chain-only antibody can be in the form of a dimer, in which two heavy chains are disulfide bonded other otherwise, covalently or non-covalently attached with each other. The heavy chain-only antibody may belong to the IgG subclass, but antibodies belonging to other subclasses, such as IgM, IgA, IgD and IgE subclass, are also included herein. In a particular embodiment, the heavy chain antibody is of the IgG1, IgG2, IgG3, or IgG4 subtype, in particular IgG1 subtype. In one embodiment, the heavy chain-only antibodies herein are used as a binding (targeting) domain of a chimeric antigen receptor (CAR).

The term "variable", as used in connection with antibodies, refers to the fact that certain portions of the antibody variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (sec Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" residues 26-32 (H1), 53-55 (H2) and 96-101 (H3) in the heavy chain variable domain; Chothia and Lesk J. Mol. Biol. 196:901-917 (1987)). "Framework Region" or "FR" residues are those variable domain residues other than the hypervariable region residues as herein defined.

Exemplary CDR designations are shown herein, however one of skill in the art will understand that a number of definitions of the CDRs are commonly in use, including the Kabat definition (see "Zhao et al. A germline knowledge based computational approach for determining antibody complementarity determining regions." Mol Immunol. 2010; 47:694-700), which is based on sequence variability and is the most commonly used. The Chothia definition is based on the location of the structural loop regions (Chothia et al. "Conformations of immunoglobulin hypervariable regions." Nature. 1989; 342:877-883). Alternative CDR definitions of interest include, without limitation, those disclosed by Honegger, "Yet another numbering scheme for immunoglobulin variable domains: an automatic modeling and analysis tool." J Mol Biol. 2001; 309:657-670; Ofran et al. "Automated identification of complementarity determining regions (CDRs) reveals peculiar characteristics of CDRs and B cell epitopes." J Immunol. 2008; 181:6230-6235; Almagro "Identification of differences in the specificity-determining residues of antibodies that recognize antigens of different size: implications for the rational design of antibody repertoires." J Mol Recognit. 2004; 17:132-143; and Padlan et al. "Identification of specificity-determining residues in antibodies." Faseb J. 1995; 9:133-139., each of which is herein specifically incorporated by reference.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antibodies of the invention include multi-specific antibodies. Multi-specific antibodies have more than one binding specificity. The term "multi-specific" specifically includes "bispecific" and "trispecific," as well as higher-order independent specific binding affinities, such as higher-order polyepitopic specificity, as well as tetravalent antibodies and antibody fragments. "Multi-specific" antibodies specifically include antibodies comprising a combination of different binding entities as well as antibodies comprising more than one of the same binding entity. The terms "multi-specific antibody," multi-specific single chain-only antibody" and "multi-specific HCAb" are used herein in the broadest sense and cover all antibodies with more than one binding specificity.

The term "valent" as used herein refers to a specified number of binding sites in an antibody molecule.

A "multi-valent" antibody has two or more binding sites. Thus, the terms "bivalent", "trivalent", and "tetravalent" refers to the presence of two binding sites, three binding sites, and four binding sites, respectively. Thus, a bispecific antibody according to the invention is at least bivalent and may be trivalent, tetravalent, or otherwise multi-valent.

A large variety of methods and protein configurations are known and used for the preparation of bispecific monoclonal antibodies (BsMAB), tri-specific antibodies, and the like.

The term "bispecific three-chain antibody like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy chain only antibody comprising an Fc portion comprising CH2 and/or CH3 and/or CH4 domains, in the absence of a CH1 domain, and an antigen binding domain that binds an epitope of a second antigen or a different epitope of the first antigen, where such binding domain is derived from or has sequence identity with the variable region of an antibody heavy or light chain. Parts of such variable region may be encoded by $V_H$ and/or $V_L$ gene segments, D and $J_H$, gene segments, or $J_L$ gene segments. The variable region may be encoded by rearranged $V_H DJ_H$, $V_L DJ_H$, $V_L J_L$, or $V_L J_L$ gene segments. A TCA protein makes use of a heavy chain-only antibody as hereinabove defined.

The term "chimeric antigen receptor" or "CAR" is used herein in the broadest sense to refer to an engineered receptor, which grafts a desired binding specificity (e.g. the antigen-binding region of a monoclonal antibody or other ligand) to membrane-spanning and intracellular-signaling domains. Typically, the receptor is used to graft the specificity of a monoclonal antibody onto a T cell to create a chimeric antigen receptos (CAR). (*J Natl Cancer Inst*, 2015; 108(7):dvj439; and Jackson et al., *Nature Reviews Clinical Oncology*, 2016; 13:370-383.) A representative CAR-T construct comprising a human VH extracellular binding domain is shown in FIG. 6.

By "human idiotype" is meant a polypeptide sequence epitope present on a human antibody in the immunoglobulin heavy and/or light chain variable region. The term "human idiotype" as used herein includes both naturally occurring sequences of a human antibody, as well as synthetic sequences substantially identical to the polypeptide found in naturally occurring human antibodies. By "substantially" is meant that the degree of amino acid sequence identity is at least about 85%-95%. Preferably, the degree of amino acid sequence identity is greater than 90%, more preferably greater than 95%.

By a "chimeric antibody" or a "chimeric immunoglobulin" is meant an immunoglobulin molecule comprising amino acid sequences from at least two different Ig loci, e.g., a transgenic antibody comprising a portion encoded by a human Ig locus and a portion encoded by a rat Ig locus. Chimeric antibodies include transgenic antibodies with non-human Fe-regions or artificial Fc-regions, and human idiotypes. Such immunoglobulins can be isolated from animals of the invention that have been engineered to produce such chimeric antibodies.

Antibody "effector functions" refer to those biological activities attributable to the Fc region (a native sequence Fc region or amino acid sequence variant Fc region) of an antibody. Examples of antibody effector functions include Clq binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoictic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (*USA*) 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

"Complement dependent cytotoxicity" or "CDC" refers to the ability of a molecule to lyse a target in the presence of complement. The complement activation pathway is initiated by the binding of the first component of the complement system (Clq) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art. Low-affinity antibodies generally bind antigen slowly and tend to dissociate readily, whereas high-affinity antibodies generally bind antigen faster and tend to remain bound.

As used herein, the "Kd" or "Kd value" refers to a dissociation constant determined by BioLayer Interferometry, using an Octet QK384 instrument (Fortebio Inc., Menlo Park, Calif.) in kinetics mode. For example, anti-mouse Fc sensors are loaded with mouse-Fc fused antigen and then dipped into antibody-containing wells to measure concentration dependent association rates (kon). Antibody dissociation rates (koff) are measured in the final step, where the sensors are dipped into wells containing buffer only. The Kd is the ratio of koff/kon. (For further details see, Concepcion, J, et al., *Comb Chem High Throughput Screen*, 12(8), 791-800, 2009).

An "epitope" is the site on the surface of an antigen molecule to which a single antibody molecule binds. Generally an antigen has several or many different epitopes and reacts with many different antibodies. The term specifically includes linear epitopes and conformational epitopes.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Polyepitopic specificity" refers to the ability to specifically bind to two or more different epitopes on the same or different target(s).

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g. mouse, rat, etc.

II. Detailed Description

Anti-BCMA Antibodies

The present invention provides a family of closely related heavy chain-only antibodies that bind to human BCMA. The antibodies of this family comprise a set of CDR sequences as defined herein and shown in FIG. 1, and are exemplified by the provided heavy chain variable region (VH) sequences of SEQ ID NOs 20 to 53 set forth in FIG. 2. The families of antibodies provide a number of benefits that contribute to utility as clinically therapeutic agent(s). The antibodies include members with a range of binding affinities, allowing the selection of a specific sequence with a desired binding affinity.

A suitable antibody may be selected from those provided herein for development and therapeutic or other use, including without limitation use as a bispecific or tri-specific antibody, or part of a CAR-T structure. Determination of affinity for a candidate protein can be performed using methods known in the art, such as Biacore measurements. Members of the antibody family may have an affinity for BCMA with a Kd of from about $10^{-6}$ to around about $10^{-11}$, including without limitation: from about $10^{-6}$ to around about $10^{-10}$; from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for modulating, e.g. blocking, a BCMA biological activity, including in vitro assays, pre-clinical models, and clinical trials, as well as assessment of potential toxicity.

Members of the antibody family herein are not cross-reactive with the BCMA protein of Cynomolgus macaque but can be engineered to provide cross-reactivity if desired.

The family of BCMA specific antibodies herein comprises a VH domain, comprising CDR1, CDR2 and CDR3 sequences in a human VH framework. The CDR sequences may be situated, as an example, in the region of around amino acid residues 26-35; 53-59; and 98-117 for CDR1, CDR2 and CDR3, respectively, of the provided exemplary variable region sequences set forth in SEQ ID NO: 20-53. It will be understood by one of skill in the art that the CDR sequences may be in different position if a different framework sequence is selected, although generally the order of the sequences will remain the same.

The antibodies of the present invention share the CDR3 amino acid sequence of SEQ ID NO: 19. The CDR1 and CDR2 sequences of the anti-BCMA antibodies of the present invention may be encompassed by the following structural formulas, where an X indicates a variable amino acid, which may be specific amino acids as indicated below.

CDR1

G F T F X1 X2 Y A    (SEQ ID NO: 55)

where
X1 is S or T;
X2 is S, N or R

CDR2

X3 X4 X5 X6 G X7 X8 X9    (SEQ ID NO: 56)

where
X3 is I or L;
X4 is S, T, I or V;
X5 is G or E;
X6 is S, G, N or D;
X7 is G, D or A;
X8 is S, T or N;
X9 is T or S.

Representative CDR1, CDR2, and CDR3 sequences are shown in FIG. 1.

In some embodiments the anti-BCMA antibody of the invention comprises a CDR1 sequence of SEQ ID NO: 1, 2, 3, or 4. In a particular embodiment, the CDR1 sequence is SEQ ID NO: 1 or SEQ ID NO: 2.

In some other embodiments the anti-BCMA antibody of the invention comprises a CDR2 sequence of any one of SEQ ID NOs: 5-18. In a particular embodiment, the CDR2 sequence is SEQ ID NO: 5.

In another embodiment, the anti-BCMA antibody of the present invention comprises a CDR1 sequence of SEQ ID NO: 1, a CDR2 sequence of SEQ ID NO: 5 and a CDR3 sequence of SEQ ID NO: 19.

In a further embodiment, the anti-BCMA antibody of the present invention comprises a CDR1 sequence of SEQ ID NO: 2, a CDR2 sequence of SEQ ID NO: 5 and a CDR3 sequence of SEQ ID NO: 19.

In further embodiments, the anti-BCMA antibody of the present invention comprises any of the heavy chain amino acid sequences of SEQ ID NOs: 20 to 53 (FIG. 2).

In some embodiments a CDR sequence of the invention comprises one, two, three or more amino acid substitutions relative to a CDR1, CDR2 and/or CDR3 sequence or set of CDR1, CDR2 and CDR3 sequences in any one of SEQ ID NOs:1 to 19 (FIG. 1). In some embodiments said amino acid substitution(s) are one or more of amino acid positions 5 and 6 of CDR1, and/or one or more of the amino acid positions of 1-4 and 6-8 of CDR2, relative to the formulas provided above. In some embodiments the CDR sequences of an anti-BCMA antibody herein have a sequence with at least 85% identity, at least 90% identity, at least 95% identity, at least 98% identify, or at least 99% identity relative to a CDR1, CDR2 and/or CDR3 sequence or set of CDR1, CDR2, and CDR3 sequences in any one of SEQ ID NOs: 1 to 19 (FIG. 1). In some other embodiments, the single chain-only anti-BCMA antibodies herein will comprise a heavy chain variable region sequence with at least 85% identity, at least 90% identity, at least 95% identity, at least 98% identity, or at least 99% identity to the heavy chain variable region sequences shown in FIG. 2.

In some embodiments, bispecific or multispecific antibodies are provided, which may have any of the configurations discussed herein, including without limitation a three chain bispecific antibody. Bispecific antibodies comprise at least the heavy chain variable region of an antibody specific for a protein other than BCMA.

Where a protein of the invention is a bispecific antibody, one binding moiety is specific for human BCMA while the other arm may be specific for target cells, tumor associated antigens, targeting antigens, e.g. integrins, etc., pathogen antigens, checkpoint proteins, and the like. Target cells specifically include cancer cells, such as hematologic tumors, e.g. B-cell tumors.

Various formats of bispecific antibodies are within the ambit of the invention, including without limitation single chain polypeptides, two chain polypeptides, three chain polypeptides, four chain polypeptides, and multiples thereof. The bispecific antibodies herein specifically include T-cell bispecific antibodies binding to BCMA, which is selectively expressed on plasma cells (PCs) and multiple myeloma (MM), and CD3 (anti-BCMA×anti-CD3 antibodies). Such antibodies induce potent T-cell mediated killing of cells carrying BCMA.

Pharmaceutical Compositions

It is another aspect of the present invention to provide pharmaceutical compositions comprising one or more antibodies of the present invention in admixture with a suitable pharmaceutically acceptable carrier. Pharmaceutically acceptable carriers as used herein are exemplified, but not limited to, adjuvants, solid carriers, water, buffers, or other carriers used in the art to hold therapeutic components, or combinations thereof.

Pharmaceutical composition of the antibodies used in accordance with the present invention are prepared for storage by mixing proteins having the desired degree of purity with optional pharmaceutically acceptable carriers, excipients or stabilizers (see, e.g. Remington's Pharmaceutical Sciences 16th edition, Osol, A. Ed. (1980)), such as in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Anti-BCMA antibody formulations are disclosed, for example, in U.S. Pat. No. 9,034,324. Similar formulations can be used for the proteins of the present invention.

Methods of Use

The pharmaceutical compositions herein can be used for the treatment of B-cell related disorders characterized by the expression of BCMA.

Such B-cell related disorders include B-cell and plasma cell malignancies and autoimmune disorders, including, without limitation, plasmacytoma, Hodgkins' lymphoma, follicular lymphomas, small non-cleaved cell lymphomas, endemic Burkitt's lymphoma, sporadic Burkitt's lymphoma, marginal zone lymphoma, extranodal mucosa-associated lymphoid tissue lymphoma, nodal monocytoid B cell lymphoma, splenic lymphoma, mantle cell lymphoma, large cell lymphoma, diffuse mixed cell lymphoma, immunoblastic lymphoma, primary mediastinal B cell lymphoma, pulmonary B cell angiocentric lymphoma, small lymphocytic lymphoma, B cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, or monoclonal gammopathy.

The plasma cell disorders characterized by the expression of BCMA include Multiple Myeloma (MM). MM is a B-cell malignancy characterized by a monoclonal expansion and accumulation of abnormal plasma cells in the bone marrow compartment. Current therapies for MM often cause remissions, but nearly all patients eventually relapse and die. There is substantial evidence of an immune-mediated elimination of myeloma cells in the setting of allogeneic hematopoietic stem cell transplantation; however, the toxicity of this approach is high, and few patients are cured. Although some monoclonal antibodies have shown promise for treating MM in preclinical studies and early clinical trials, consistent clinical efficacy of any monoclonal antibody therapy for MM has not been conclusively demonstrated. There is therefore a great need for new therapies, including immunotherapies for MM (see, e.g. Carpenter et al., *Chin Cancer Res* 2013, 19(8):2048-2060).

Another B-cell disorder involving plasma cells i.e. expressing BCMA is systemic lupus erythematosus (SLE), also known as lupus. SLE is a systemic, autoimmune disease that can affect any part of the body and is represented with the immune system attacking the body's own cells and tissue, resulting in chronic inflammation and tissue damage. It is a Type III hypersensitivity reaction in which antibody-immune complexes precipitate and cause a further immune response (Inaki & Lee, *Nat Rev Rheumatol* 2010; 6: 326-337).

The antibodies of the present invention can be used to develop therapeutic agents for the treatment of MM, SLE, and other B-cell disorders characterized by the expression of BCMA, such as those listed above.

In one embodiment, the antibodies herein can be in the form of heavy chain-only anti-BCMA antibody-CAR structures, i.e. heavy chain-only anti-BCMA antibody-CAR-transduced T cell structures.

Effective doses of the compositions of the present invention for the treatment of disease vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subject's response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage the agent may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the antibodies and antibody structures described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in humans. The dosage of the antibodies described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents and formulations thereof, of the invention and instructions for use. The kit can further contain a least one additional reagent, e.g. a chemotherapeutic drug, etc. Kits typically include a label indicating the intended use of the contents of the kit. The term label includes any writing, or recorded material supplied on or with the kit, or which otherwise accompanies the kit.

The invention now being fully described, it will be apparent to one of ordinary skill in the art that various changes and modifications can be made without departing from the spirit or scope of the invention.

EXAMPLES

Example 1

Genetically Engineered Rats Expressing Heavy Chain-Only Antibodies

A 'human-rat' IgH locus was constructed and assembled in several parts. This involved the modification and joining of rat C region genes downstream of human $J_H$s and subsequently, the upstream addition of the human $V_H6$-D-segment region. Two BACs with separate clusters of human $V_H$ genes [BAC6 and BAC3] were then co-injected with the BAC termed Georg, encoding the assembled and modified region comprising human $V_H6$, all Ds, all $J_H$s, and modified rat Cγ2a/1/2b ($\Delta C_H 1$).

Transgenic rats carrying artificial heavy chain immunoglobulin loci in unrearranged configuration were generated. The IgG2a($\Delta C_H 1$)., igG1($\Delta C_H 1$)., IgG2b($\Delta C_H 1$) genes lacked the $C_H 1$ segment. The constant region genes IgE, IgA and 3' enhancer were included in Georg BAC. RT-PCR and serum analysis (ELISA) of transgenic rats revealed productive rearrangement of transgenic immunoglobulin loci and expression of heavy chain only antibodies of various isotypes in serum. Transgenic rats were cross-bred with rats with mutated endogenous heavy chain and light chain loci previously described in US patent publication 2009/0098134 A1. Analysis of such animals demonstrated inactivation of rat immunoglobulin heavy and light chain expression and high level expression of heavy chain antibodies with variable regions encoded by human V, D, and J genes Immunization of transgenic rats resulted in production of high titer serum responses of antigen-specific heavy chain antibodies. These transgenic rats expressing heavy chain antibodies with a human VDJ region were called UniRats.

Example 2

Immunization
Immunization with Recombinant Extracellular Domain of BCMA.

Twelve UniRat animals (6 HC27, 6 HC28) were immunized with recombinant human BCMA protein. The animals were immunized according to standard protocol using a Titermax/Alhydrogel adjuvant. Recombinant extracellular domain of BCMA was purchased from R&D Systems and was diluted with sterile saline and combined with adjuvant. The immunogen was combined with Titermax and Alhydrogel adjuvants. The first immunization (priming) with immunogen in Titermax was administered in the left and right legs. Subsequent boosting immunizations were done in the presence of Alhydrogel and three days before harvest boosts were performed with immunogens in PBS. Serum was collected from rats at the final bleed to determine serum titers.

Serum Titer Results

Serum titer summary information is shown in FIGS. 4 and 5. For half of the animals, binding activity for a single 1:500 serum titer dilution was tested by ELISA against a huBCMA+Fc protein and a cynoBCMA+Fc protein produced in eukaryotic cells and two human BCMA proteins from E. coli and wheat germ, respectively. In addition, serum samples were tested against two off-target proteins, HSA and human IgG1. In addition, serum from all 12 animals was assayed for binding to NCI-H929 cells (BCMA+, lambda−).

Among this group of animals, we observed a significant spread in serum reactivity levels to NCI-H929 cells (BCMA+, lambda−). The relevance of these results is confirmed by the ELISA binding data generated for a subset of the animals. Some general Fc-specific reactivity is observed for a number of the animals, but those that look the most promising also show high apparent titer in the assays against untagged human BCMA from alternative sources (E. coli, wheat germ) indicating significant BCMA ECD-specific binding activity. Positive signal for binding to the cynoBCMA+Fc protein may reflect binding to either the ECD or the Fc portion of the molecule that is also included on the human immunogen. In both assay types, analysis of serum taken from these animals prior to immunization showed no reactivity to the immunogen or off target protein.

Example 3

Gene Assembly, Expression and Binding Assays 309 cDNAs encoding heavy chain only antibodies highly expressed in lymph node cells were selected for gene assembly and cloned into an expression vector. Subsequently, these 309 heavy chain sequences were expressed in HEK cells as UniAb heavy chain only antibodies (CH1 deleted, no light chain). Binding results including amino acid sequences for 34 VH regions tested can be found in the BCMA_FAM2_DATA.

Supernatants of two antibodies were tested for binding in a standard ELISA assay to a human BCMA. Binding to recombinant BCMA protein was determined by ELISA using human BCMA ECD obtained from Abcam (ab50089). The BCMA ECD protein was used at a concentration of 2 μg/mL to capture UniAbs at 50 ng/mL. Binding of UniAbs was detected with a goat anti-human IgG HRP conjugated antibody (ThermoFisher 31413). All antibodies were diluted in 1×TBS with 0.05% Tween-20 and 1% dry milk powder.

Off-target binding to Baculo Virus Protein Extract (BVP) was conducted by ELISA as above, with the modification of using 1×PBS and 1% dry milk powder for the diluent. BVP extract was obtained from INSERM (Nantes, France). Binding to baculovirus particles (>5× over background in our assay) is thought to indicate low-affinity interactions with human tissues which correlates with reduced half-lives of antibodies in humans and monkeys (Hotzcl et al., mAbs 4:6, p 753-760, 2012). Off-target binding of human IgG1 was assessed by ELISA using the UniAbs to capture human IgG1 kappa followed by detection of the kappa chain with a goat anti-human kappa HRP conjugated antibody (Southern Biotech 2060-05).

Supernatants of all antibodies were also tested by flow cytometry for binding to RPMI-8226 cells (BCMA+, lambda+) and H929 cells (BCMA+, lambda−). The samples were measured by flow cytometry using a Guava easyCyte 8HT instrument from EMD Millipore and analyzed using guavaSoft. Bound antibodies were detected with goat anti-human IgG F(ab')$_2$ conjugated to PE (Southern Biotech 2042-09). All antibodies were diluted in PBS with 1% BSA. Positive staining was determined by comparison to staining with a human IgG1 isotype control. The NCI-H929 and RPMI-8226 cell lines are human multiple myeloma lines expressing human BCMA, which were obtained from the American Type Culture Collection (ATCC) and cultured according to ATCC recommendations.

Two UniAbs were also evaluated for the ability to block APRIL (ligand)/BCMA (receptor) binding in a recombinant protein ELISA-style assay. To evaluate blocking of the receptor/ligand interaction between BCMA and APRIL, recombinant human BCMA (Sino Biological 10620-H03H) was directly coated on plates followed by incubation with a dilution series of each UniAb. HA-tagged recombinant APRIL protein (RnD Systems 5860-AP-010) was then incubated with the BCMA/antibody complexes and binding of APRIL to BCMA was detected using a chicken anti-HA antibody conjugated to HRP (Abcam ab1190). A RnD systems anti-BCMA antibody (AF193) was used as a positive control for BCMA/APRIL blocking.

An additional off-target binding assay was run on intact baculovirus particles (BVPs) though none of the tested UniAbs showed positive binding.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A heavy chain-only antibody binding to human B-Cell Maturation Antigen (BCMA) comprising a heavy chain variable region comprising:
   (a) a CDR1 sequence comprising SEQ ID NO: 1, a CDR2 sequence comprising SEQ ID NO: 5, and a CDR3 sequence comprising SEQ ID NO: 19; or
   (b) a CDR1 sequence comprising SEQ ID NO: 2, a CDR2 sequence comprising SEQ ID NO: 54, and a CDR3 sequence comprising SEQ ID NO: 19;
   in a human VH framework.

2. The heavy chain-only antibody of claim 1, further comprising a heavy chain constant region sequence in the absence of a CH1 sequence.

3. The heavy chain-only antibody of claim 1, which is in a CAR-T format.

4. The heavy chain-only antibody of claim 1, which is present in a CAR-transduced T-cell.

5. A pharmaceutical composition comprising the heavy chain-only antibody of claim 1.

6. The heavy chain-only antibody of claim 1, wherein the heavy chain variable region comprises a CDR1 sequence comprising SEQ ID NO: 1, a CDR2 sequence comprising SEQ ID NO: 5, and a CDR3 sequence comprising SEQ ID NO: 19, in a human VH framework.

7. The heavy chain-only antibody of claim 6, wherein the heavy chain variable region has at least 95% sequence identity to SEQ ID NO: 20.

8. The heavy chain-only antibody of claim 7, wherein the heavy chain variable region comprises SEQ ID NO: 20.

9. The heavy chain-only antibody of claim 6, further comprising a heavy chain constant region sequence in the absence of a CH1 sequence.

10. The heavy chain-only antibody of claim 6, which is in a CAR-T format.

11. The heavy chain-only antibody of claim 6, which is present in a CAR-transduced T-cell.

12. The heavy chain-only antibody of claim 1, wherein the heavy chain variable region comprises a CDR1 sequence comprising SEQ ID NO: 2, a CDR2 sequence comprising SEQ ID NO: 54, and a CDR3 sequence comprising SEQ ID NO: 19, in a human VH framework.

13. The heavy chain-only antibody of claim 12, wherein the heavy chain variable region has at least 95% sequence identity to SEQ ID NO: 21.

14. The heavy chain-only antibody of claim 13, wherein the heavy chain variable region comprises SEQ ID NO: 21.

15. The heavy chain-only antibody of claim 12, further comprising a heavy chain constant region sequence in the absence of a CH1 sequence.

16. The heavy chain-only antibody of claim 12, which is in a CAR-T format.

17. The heavy chain-only antibody of claim 12, which is present in a CAR-transduced T-cell.

* * * * *